(12) United States Patent
Chen et al.

(10) Patent No.: US 8,567,406 B2
(45) Date of Patent: Oct. 29, 2013

(54) ADJUSTABLE ORAL INTERFACE AND METHOD TO MAINTAIN UPPER AIRWAY PATENCY

(75) Inventors: Chung-Chu Chen, Hsinchu (TW); Marina Sirota, San Francisco, CA (US)

(73) Assignee: Somnics, Inc., San Jose, CA (US)

( * ) Notice: Subject to any disclaimer, the term of this patent is extended or adjusted under 35 U.S.C. 154(b) by 285 days.

(21) Appl. No.: 13/012,591

(22) Filed: Jan. 24, 2011

(65) Prior Publication Data

US 2011/0180075 A1 Jul. 28, 2011

Related U.S. Application Data

(60) Provisional application No. 61/298,083, filed on Jan. 25, 2010.

(51) Int. Cl.
*A61F 5/56* (2006.01)

(52) U.S. Cl.
USPC .......................................... 128/848

(58) Field of Classification Search
USPC ............ 128/846, 848, 857, 859–862, 200.24, 128/200.26, 206.29, 207.11, 207.14, 128/205.19; 602/902; 433/6, 7, 18, 20–22, 433/91, 93, 94, 96, 136–141; 600/206, 208, 600/210, 216, 235, 236, 237, 238, 239, 600/242; 482/11
See application file for complete search history.

(56) References Cited

U.S. PATENT DOCUMENTS 1,354,652 A * 10/1920 Jefferies ...................... 128/857

2,600,025 A * 6/1952 Sage ........................ 606/204.15
4,114,626 A 9/1978 Beran
4,711,237 A * 12/1987 Kaiser ........................... 128/859

(Continued)

FOREIGN PATENT DOCUMENTS

CN 2360112 Y 1/2000
CN 2455230 Y 10/2001

(Continued)

OTHER PUBLICATIONS

Damjanovic et al. "Compliance in sleep apnoea Therapy: influence of home care support and pressure mode", European respiratory journal, vol. 33, No. 4, Jan. 7, 2009, pp. 804-811.

(Continued)

*Primary Examiner* — Patricia Bianco
*Assistant Examiner* — Raymond E Harris
(74) *Attorney, Agent, or Firm* — Birch, Stewart, Kolasch & Birch, LLP

(57) ABSTRACT

An oral apparatus and a method capable of alleviating or curing snore and obstructive sleep apnea by applying a negative pressure through a mini oral interface to the oral cavity are provided. The mini oral interface creates a secure connection to mouth and prevents disengaging from patient's mouth during sleeping. The negative pressure pulls the tongue toward upper palate and also pulls the soft palate forward. By moving the tongue and the soft tissue in a forward direction, the patency of the upper airway near the pharynx is maintained to prevent sleep-disordered breathing. The negative pressure will pull the lips inward to close the mouth preventing air from entering the oral cavity from atmosphere. The negative pressure will also pull the soft palate into contact with the rear surface of the tongue to create a seal that prevents the air from entering the oral cavity through the nasal airway.

14 Claims, 32 Drawing Sheets

(56) References Cited

U.S. PATENT DOCUMENTS

| | | | | |
|---|---|---|---|---|
| 4,817,636 A * | 4/1989 | Woods | | 128/848 |
| 4,825,881 A * | 5/1989 | Bessler | | 128/859 |
| 4,883,072 A * | 11/1989 | Bessler | | 128/857 |
| 5,957,133 A | 9/1999 | Hart | | |
| 6,016,807 A * | 1/2000 | Lodge | | 128/848 |
| 6,076,526 A * | 6/2000 | Abdelmessih | | 128/848 |
| 6,089,232 A * | 7/2000 | Portnoy et al. | | 128/848 |
| 7,032,598 B2 * | 4/2006 | Portnoy | | 128/848 |
| 7,185,654 B2 * | 3/2007 | Haddix et al. | | 128/848 |
| 7,802,572 B2 * | 9/2010 | Hahne | | 128/206.19 |
| 7,918,222 B2 * | 4/2011 | Chen | | 128/200.24 |
| 2004/0089310 A1 | 5/2004 | Portnoy | | |
| 2005/0166928 A1 | 8/2005 | Jiang | | |
| 2006/0019216 A1 * | 1/2006 | Priluck et al. | | 433/140 |
| 2006/0096600 A1 | 5/2006 | Witt et al. | | |

FOREIGN PATENT DOCUMENTS

| | | |
|---|---|---|
| CN | 101143115 A | 3/2008 |
| FR | 2 574 657 A1 | 6/1986 |
| WO | WO 99/61089 A1 | 12/1999 |
| WO | WO 2007/075491 A2 | 7/2007 |

OTHER PUBLICATIONS

Ferguson et al. "Oral Appliances for Snoring and Obstructive Sleep Apnea: A RevieW", Sleep, vol. 29, No. 2, 2006, pp. 244-262.

Flemons, "Clinical Practice", Obstructive Sleep Apnea, N Engl J Med, vol. 347, No. 7, Aug. 15, 2002, pp. 498-504.

Giles et al. "Continuous positive airways pressure for obstructive sleep apnoea in adults (Review)", The Cochrane Library 2006, Issue 2, pp. 1-80.

Gotsopoulos et al., "Oral Appliance Therapy Improves Symptoms in Obstructive Sleep Apnea", Am J Respir Crit Care Med, vol. 166, 2002, pp. 743-748.

Haentjens et al., "The Impact of Continuous Positive Airway Pressure on Blood Pressure in Patients with Obstructive Sleep Apnea Syndrome", Arch Intern Med, vol. 167, Apr 23, 2007, pp. 757-765.

Hoy et al., "Can Intensive Support Improve Continuous Positive Airway Pressure Use in Patients with the Sleep Apnea/Hypopnea Syndrome?", Am J Respir Crit Care Med, vol. 159, 1999, pp. 1096-1100.

Lawati et al., "Epidemiology, Risk Factors, and Consequences of Obstructive Sleep Apnea and Short Sleep Duration", Progress in Cardiovascular Disease, vol. 51, No. 4, Jan./Feb. 2009, pp. 285-293.

Sundaram et al., "Surgery for obstructive sleep apnoea in adults (Review)", The Cochrane Library 2009, Issue 1, pp. 1-72.

Won et al., "Surgical Treatment of Obstructive Sleep Apnea", Proc Am Thorac Soc, vol. 5, 2008, pp. 193-199.

Young et al., "Risk Factors for Obstructive Sleep Apnea in Adults", Journal of American Medical Association, vol. 291, No. 16, Apr. 28, 2004, pp. 2013-2016.

Young et al., "The Occurrence of Sleep-Disordered Breathing Among Middle-Aged Adults", N Engl J Med, vol. 328, No. 17, Apr. 29, 1993, pp. 1230-1235.

Douglas et al., "Chapter 259. Sleep Apnea," Harrison's Principles of Internal Medicine, 17th Ed., Prior to Sep. 8, 2010, pp. 1-7.

* cited by examiner

ADJUSTABLE ORAL INTERFACE AND METHOD TO MAINTAIN UPPER AIRWAY PATENCY

CROSS REFERENCE TO RELATED APPLICATIONS

This nonprovisional application claims the benefit of U.S. Provisional Application No. 61/298,083 filed on Jan. 25, 2010. The entire contents of the above application is hereby incorporated by reference.

BACKGROUND OF THE INVENTION

1. Field of the Invention

The present invention is related to methods and systems capable of reducing obstruction of the upper airway in obstructive sleep apnea (OSA) and snore patients. More particularly, the present invention relates to an oral apparatus that prevents mouth breathing and also provides negative pressure in the oral cavity.

2. Prior Art

Obstructive sleep apnea (OSA) is a condition in which repeated collapses in the patient's airway during inhalation causes a cessation of breathing during sleep. During inhalation, air pressure in the lungs and respiratory passages is reduced. If during this time, the tone of the muscles in the upper-airway is reduced, the airway tends to collapse. As the airway begins to occlude prior to an apnea episode, the patient often begins to snore. Snoring is an effort to try to combat the collapsed airway. These obstructions occur in different locations along the respiratory pathway in different patients, but the two common locations are the oropharynx or the nasopharynx.

People with moderate to severe OSA experience daytime sleepiness, fatigue, and poor concentration. In addition to these immediate problems, research has shown that patients with OSA use more medical resources, have an increased risk of medical disability, and finally have a higher mortality rate. Patients with severe OSA are estimated to have a three to six fold increased risk of mortality considering all causes. OSA is also implicated in many cardiovascular conditions, such as systemic hypertension and some degree of pulmonary hypertension. It is associated with an increased risk for myocardial infarction, cerebrovascular disease, and cardiac arrhythmia. OSA causes excessive daytime sleepiness due to interrupted sleeping pattern at night which leads to inability to concentrate. Patients' daily functions are impaired as their neuro-cognitive function is compromised. They are more likely to make errors and run into accidents. Therefore, OSA is a significant medical condition with serious negative outcomes if left untreated.

There are several current treatment options for OSA patients. Oral appliances are used to treat mild OSA, but they often don't work well and cause damage to gums and teeth. Several types of surgery are used to treat OSA, however, surgical options are invasive, expensive and painful with recovery periods up to 6 months. The most common treatment for moderate to severe sleep apnea in adults is CPAP, which has 96% market share in OSA therapeutics. A CPAP machine consists of a mask, a pump and a humidifier. The device continuously blows pressurized air into the patient's nose to keep the airway open during sleep. CPAP is quite effective; however, it has unpleasant side effects such as dry throat and nose congestion. Patients who use CPAP often feel bloated in the morning and experience headaches. The machine is noisy and uncomfortable for the user and their partner. CPAP is currently the first-line and gold standard treatment, but it suffers low compliance due to significant side effects.

It has been proposed to apply a negative pressure to the patient's oral cavity to pull the tongue and soft palate forward to maintain the patency of the airway, as an improvement over CPAP, for example, U.S. patent and Patent Publication Nos. U.S. Pat. No. 5,957,133, 2005/0166928, and 2006/0096600. While promising in theory, these prior arts comprise relatively large structures to engage the teeth and/or to retain the tongue. Moreover, negative pressure is applied directly on the soft tissues of the tongue to hold the tongue within the cavity. These approaches tend to occupy a lot of space in the oral cavity, which may cause discomfort and damage to large area of teeth, gum, and soft tissues. At the same time, the presence of such larger devices may induce excess saliva secretion and elicit the gag reflex. The other major disadvantage of these approaches is that the oral devices are anatomically dependent, requiring special technicians to customize the interface for each individual patient.

Therefore, it is one objective of the present invention to provide alternative and improved methods and apparatus for treating obstructive sleep apnea and snoring. It is another objective of the present invention to provide minimally intrusive methods and apparatus with components that are comfortable and convenient to use. It is still an objective of the present invention to provide methods and apparatus that avoid contacting the portions of the oral cavity that cause discomfort, induce excess saliva, and trigger the gag reflex. The methods and apparatus should be simple to implement and to significantly improve patency of a patient's airway during sleep. At least some of these objectives will be met by the inventions described hereinafter.

SUMMARY OF THE INVENTION

The present invention provides an oral apparatus and method capable of alleviating or curing snoring and obstructive sleep apnea by creating a small oral interface and applying negative pressure through the small interface to the oral cavity. The small interface creates a secure connection to mouth and prevents disengaging from patient's mouth during sleep. The negative pressure pulls the tongue toward upper palate and also pulls the soft palate forward. By moving the tongue and the soft tissue in a forward direction, the patency of the upper airway near the pharynx is maintained to prevent sleep-disordered breathing. The oral apparatus will pull the lips inward to close the mouth preventing air from entering the oral cavity from atmosphere. The negative pressure will also pull the soft palate into contact with the rear surface of the tongue to create a seal that prevents the air entering the oral cavity through the nasal airway. This therapy connected to a negative pressure source but only required partial active pumping time and minimal airflow, which is very energy-efficient and quiet.

In one embodiment, the present invention provides an oral apparatus, comprising of: a upper component and a lower component, which can be temporarily attached to the skin around upper lip and lower lip separately; a connector to connect and disconnect, as well as control the distance between upper and lower components. The upper and lower components may only be applied to lip region away from the opening of the mouth to allow for the mouth to open. The closing of the mouth will be attained by the lips with the help of the pulling force exerted by the connector to the upper and lower components. The connector may comprise of a female connector on one attaching component and a male connector on the other attaching component so that the connectors can be engaged and disengaged to close and release the mouth. The opening of mouth is not occluded by the upper and lower attaching components of the interface which may allow the user to exhale air through the mouth even when the male and female connectors are engaged. The user can also temporarily manually disengage the connector assembly to allow the user to drink water, speak or perform other activities.

The present invention can be used in combination with constant positive airway pressure devices, oral appliances, or other sleep apnea therapies to prevent mouth breathing.

In another embodiment, the present invention provides a method, comprising of: applying an upper attaching component to the skin around the upper lip and a lower attaching component to the skin around the lower lip without occluding the opening of the mouth; using a connector to engage and disengage as well as control the distance between the upper and lower attaching components; providing a conduit with a complementary part which interlocks with said attaching components; applying a negative pressure to oral cavity via the said conduit.

BRIEF SUMMARY OF THE DRAWINGS

The objects, spirits and advantages of the preferred embodiments of the present invention will be readily understood by the accompanying drawings and detailed descriptions, wherein:

FIG. 14A to FIG. 14E show schematic diagrams of an oral apparatus according to the fourteenth embodiment of the present invention to use upper and lower attaching components with a loop and hooks to close the mouth;

DETAILED DESCRIPTION OF THE INVENTION

Figure 1A:
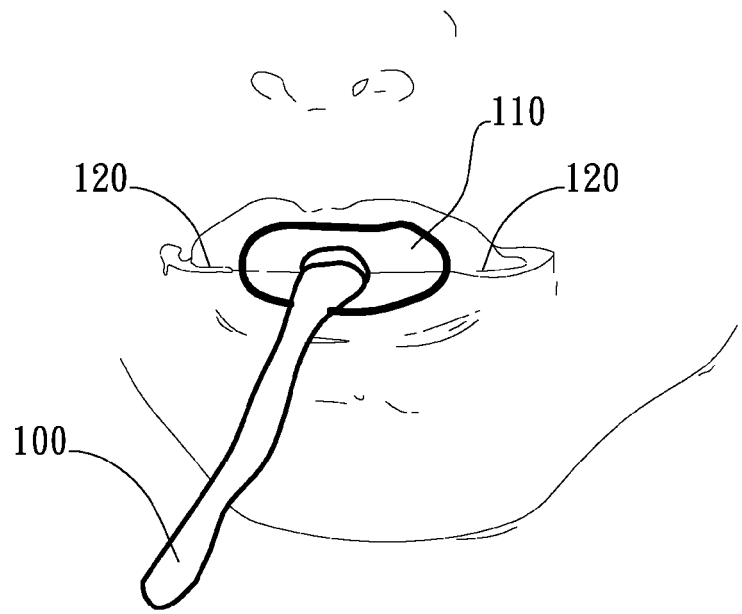
FIG. 1A to FIG. 1F show schematic diagrams of an oral apparatus according to the first embodiment of the present invention to deliver negative pressure using a tube and adhesive tape of different sizes and shapes to prevent the mouth from opening.
Figure 1B:
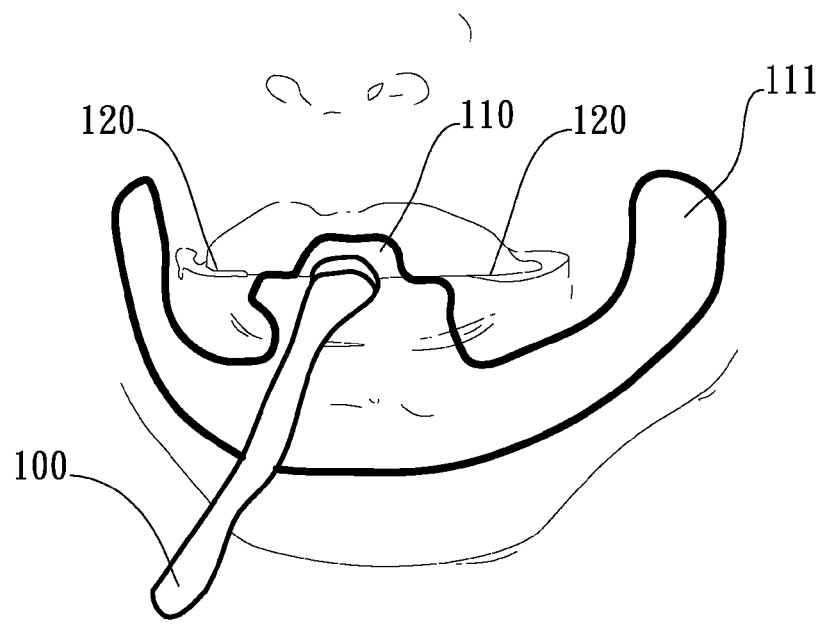
Figure 1C:
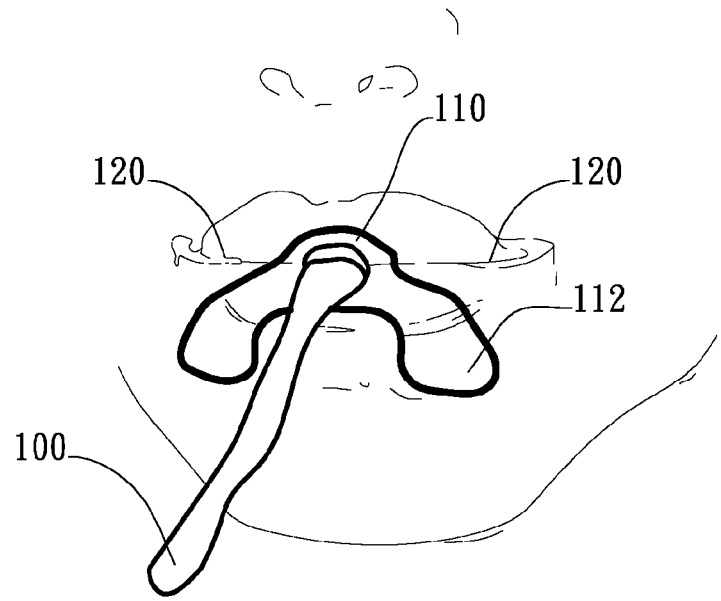
Figure 1D:
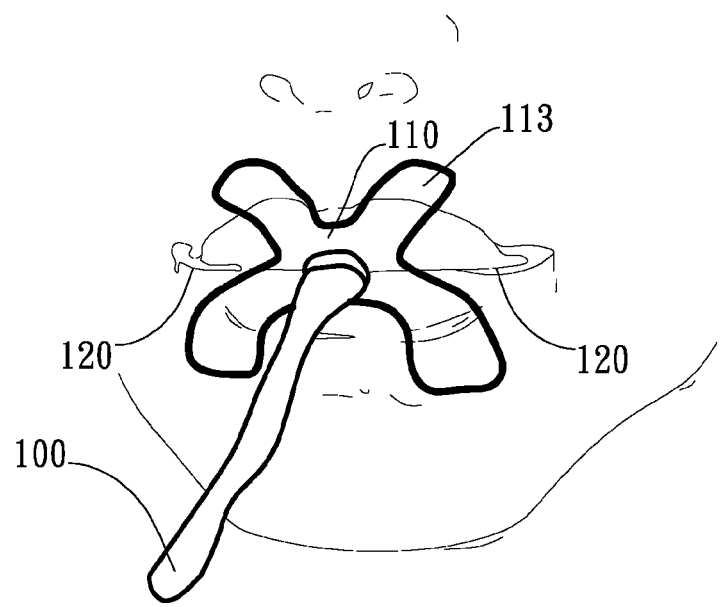
Figure 1E:
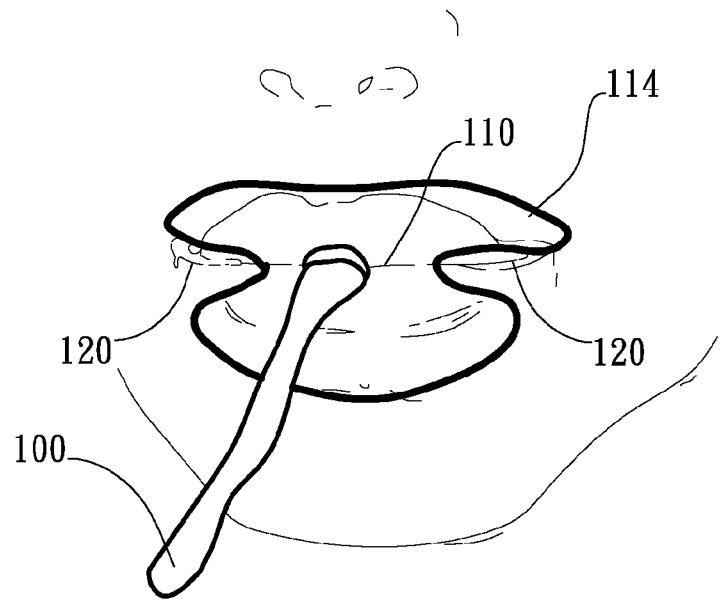

Reference will now be made in detail to the present exemplary embodiments, examples of which are illustrated in the accompanying drawings. Wherever possible, the same reference numbers are used in the drawings and the description to refer to the same or like parts.

Figure 1F:
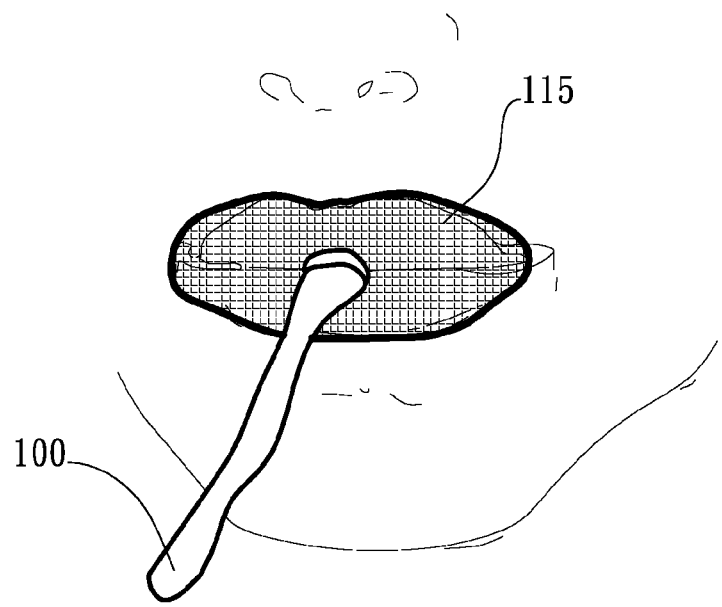

Please refer to FIG. 1A to FIG. 1F. FIG. 1A demonstrates the front view of an oral apparatus according to the first embodiment of the present invention. The oral apparatus comprises of a central adhesive tape 110 which is smaller than the mouth opening in width and provides uncovered regions 120 to allow partially opening of the mouth. The central adhesive tape 110 can further have upper and/or lower extensions to adhere to upper lip region and lower lip region to increase adhesion force. The central adhesive tape 110 can be of various thickness and flexibility, and is capable of adhering firmly to the skin. Potential materials of the central adhesive tape 110 include silicone, flexible plastic, latex, gel, hydrogel, acrylic gel as well as other materials coated with an adhesive substance. The closing of the mouth at the uncovered region 120 where the central adhesive tape 110 does not cover will be attained by the lips with the help of the pulling force exerted by the central adhesive tape 110. As shown by extensions 111, 112, 113, and 114 in FIGS. 1B, 1C, 1D and 1E, respectively, in the present embodiment, the adhesive tape structure can be designed to have various shapes to increase the holding force of the adhesive tapes and prevent the mouth from opening. The uncovered regions 120 are not covered by the adhesive tapes to allow for the mouth to open if needed. FIG. 1F demonstrates the front view of yet another oral apparatus according to the first embodiment of the present invention.

The adhesive tape 115 may be a breathable tape with arrays of venting holes that covers the opening area of the mouth. The uncovered regions 120 and the venting holes on adhesive tapes (110, 111, 112, 113, 114, and 115) may allow the user to exhale air through the mouth if needed. The oral apparatus can further comprise a fluid conduit 100 and a negative pressure source (not shown). The central adhesive tape 110 can be temporarily attached to the skin as well as to the fluid conduit 100 and is used to secure the fluid conduit 100 and to keep the mouth closed. The fluid conduit 100 has a first opening end connecting to the central adhesive tape 110 and extending into the user's mouth. The central adhesive tape 110 may only be applied to lip region around the fluid conduit 100 (as shown in FIG. 1A) not covering the whole mouth, and preserving one's ability to open uncovered regions 120 of the mouth. Once the central adhesive tape 110 and the fluid conduit 100 are physically connected, the pressure source can draw air out of oral cavity and thus produce a negative pressure environment to pull the tongue, soft palate and other soft tissue forward to maintain the airway patency. The present invention can be used in combination with constant positive airway pressure devices, oral appliances, or other sleep apnea therapies to prevent mouth breathing.

Figure 2A:
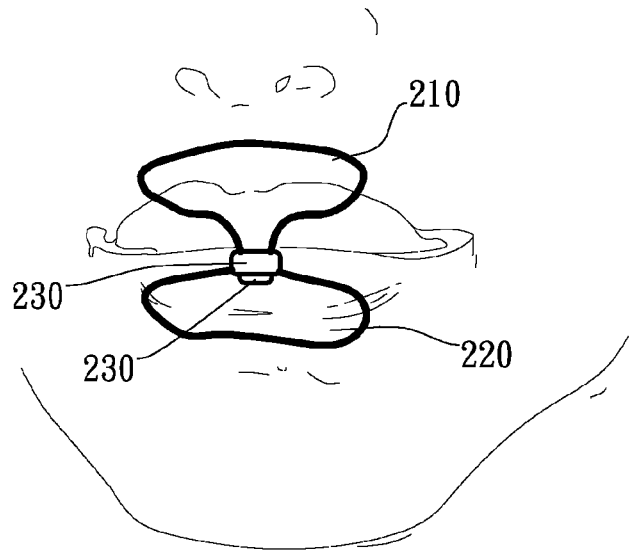
FIG. 2A and FIG. 2D show schematic diagrams of an oral apparatus according to the second embodiment of the present invention to use upper and lower attaching components with mechanical connectors to close the mouth.
Figure 2B:
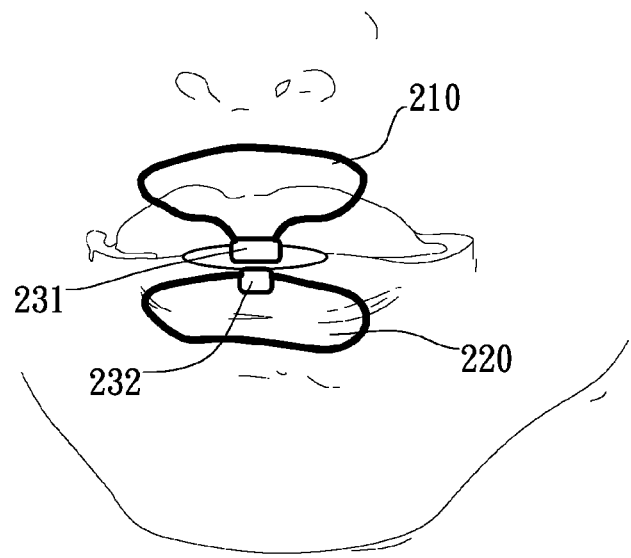
Figure 2C:
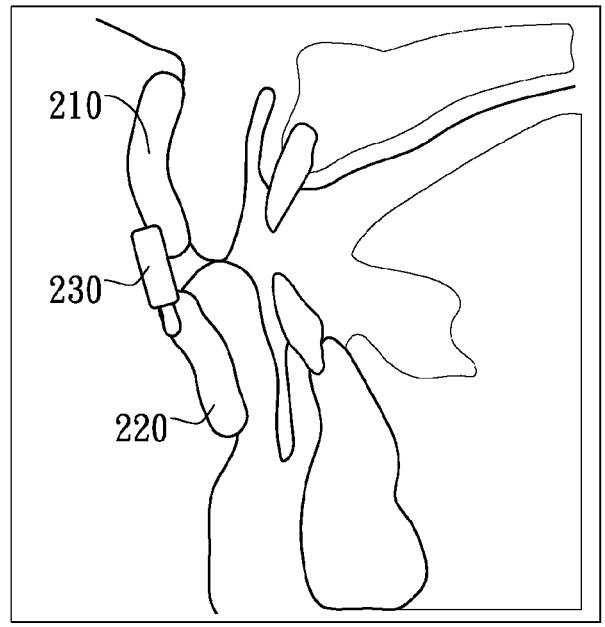
Figure 2D:
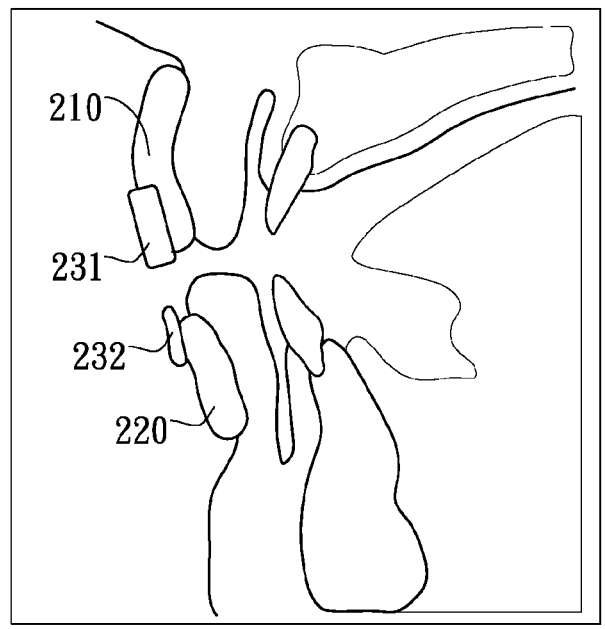

Please refer to FIG. 2A to FIG. 2D. FIG. 2A demonstrates the front view of an oral apparatus according to the second embodiment of the present invention. The oral apparatus comprises of an upper attaching component 210 and a lower attaching component 220. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. The adhesive upper and lower attaching components 210 and 220 can be temporarily attached to the skin around the upper and lower lips, respectively. The oral apparatus also has a connector 230 to control the distance between the upper attaching component 210 and the lower attaching component 220 in order to close the mouth. The upper and lower attaching components 210, 220 may only be applied to lip region away from the opening of the mouth to allow for the mouth to open. The closing of the mouth will be attained by the lips with the help of the pulling force exerted by the connector 230 to the upper and lower attaching components 210 and 220. As shown in FIG. 2B, the connector 230 may comprise of a female connector 231 on one attaching component and a male connector 232 on the other attaching component so that the connectors can be engaged and disengaged to close and release the mouth. The opening of mouth is not occluded by the upper and lower attaching components 210, 220 of the oral apparatus which may allow the user to exhale air through the mouth even when the male and female connectors 231 and 232 are engaged. The user can also temporarily manually disengage the connector assembly 230 to allow the user to drink water, speak or perform other activities. FIG. 2C and FIG. 2D demonstrate the side view of the engaged and disengaged apparatus respectively. The present invention can be used in combination with constant positive airway pressure devices, oral appliances, or other sleep apnea therapies to prevent mouth breathing.

Figure 3A:
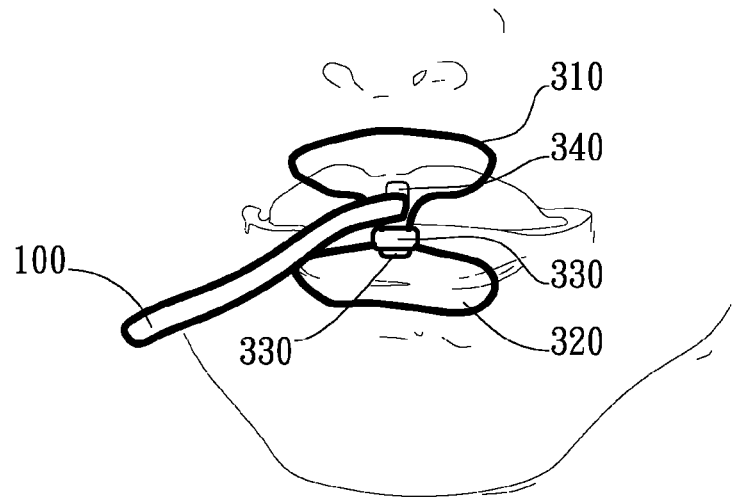
FIG. 3A to FIG. 3D show schematic diagrams of an oral apparatus according to the third embodiment of the present invention to use upper and lower attaching components with mechanical connectors to close the mouth while delivering oral negative pressure.
Figure 3B:
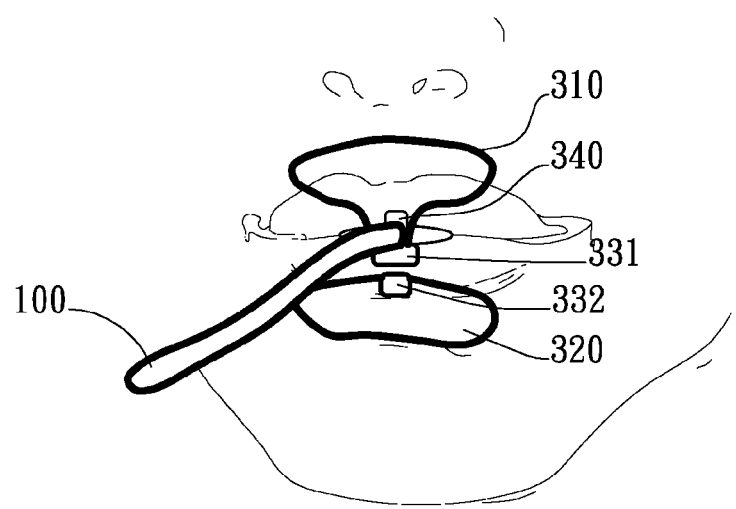
Figure 3C:
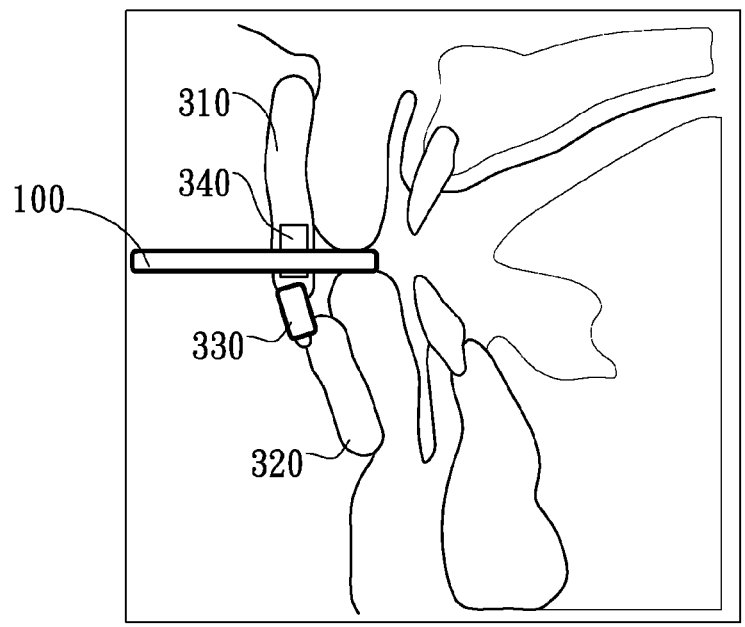
Figure 3D:
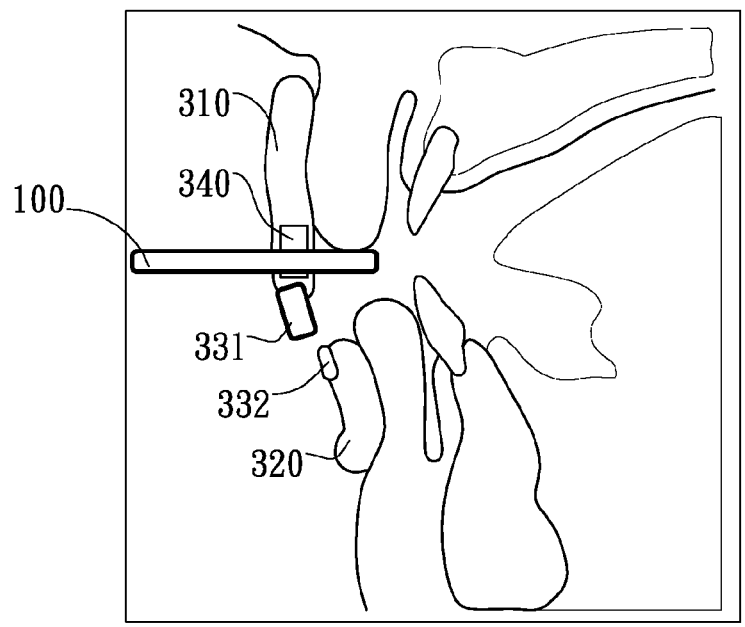

Please refer to FIG. 3A to FIG. 3D. FIG. 3A demonstrates the front view of an oral apparatus according to the third embodiment of the present invention. The oral apparatus comprises of an upper attaching component 310 and a lower attaching component 320. One of the attaching components may have a conduit engaging slot 340. The first end of a fluid conduit 100 can pass through the conduit engaging slot 340 and enter the oral cavity. The second end of the fluid conduit 100 is connected to a negative pressure source (not shown). The fluid conduit 100 may slide up or down along the conduit engaging slot 340 to accommodate variation of distance between the mouth opening and the attaching component. The upper and lower attaching components 310 and 320 can be adhesive tapes of various thickness and flexibility, and is capable of adhering firmly to the skin. Potential materials of the upper attaching component 310 and the lower attaching component 320 include silicone, flexible plastic, latex, gel, hydrogel, acrylic gel as well as other materials coated with an adhesive substance. The adhesive upper and lower attaching components 310 and 320 can be temporarily attached to the skin around the upper and lower lips, respectively. The oral apparatus also has a connector 330 to control the distance between the upper attaching component 310 and the lower attaching component 320 in order to close the mouth. The upper and lower attaching components 310, 320 may only be applied to the lip region away from the opening of the mouth to enable the user to open the mouth. The closing of the mouth will be attained by the lips with the help of the pulling force exerted by the connector 330 between the upper and lower attaching components 310 and 320. As shown in FIG. 3B, the connector 330 may comprise of a female connector 331 on one attaching component and a male connector 332 on the other attaching component so that the connectors can be engaged and disengaged to close and release the mouth. The opening of mouth is not occluded by the upper and lower attaching components 310, 320 which may allow the user to exhale air through the mouth even when the male and female connectors 331 and 332 are engaged. The user can also temporarily manually disengage the connector assembly 330 to allow the user to drink water, speak or perform other activities. FIG. 3C and FIG. 3D demonstrate the side view of the engaged and disengaged apparatus respectively. Once the two attaching components, 310 and 320, and the fluid conduit 100 are physically engaged with the conduit engaging slot 340, the negative pressure source can draw air out of oral cavity and thus produce a negative pressure environment to pull the tongue, soft palate and other soft tissue forward to maintain the airway patency reducing snoring and apnea episodes.

Figure 4A:
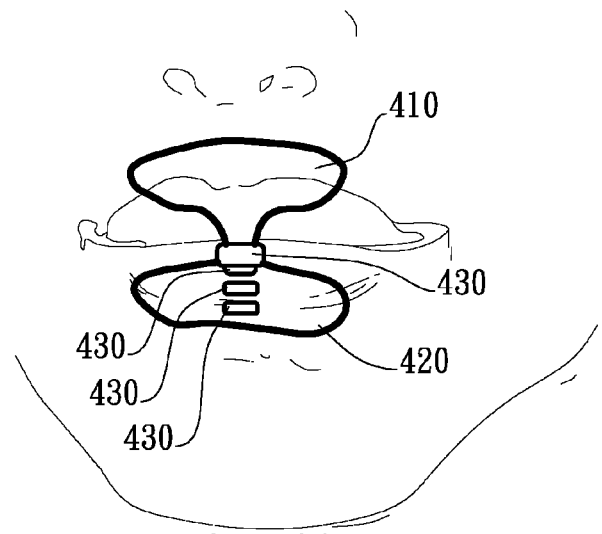
FIG. 4A to FIG. 4E show schematic diagrams of an oral apparatus according to the fourth embodiment of the present invention to use upper and lower attaching components with adjustable mechanical connectors to close the mouth.
Figure 4B:
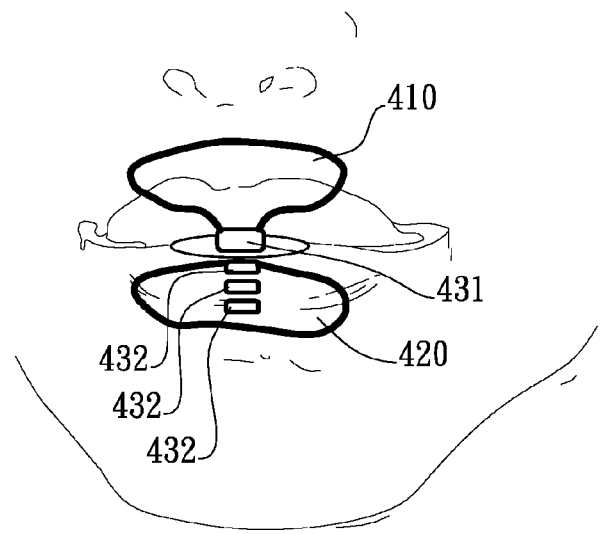
Figure 4C:
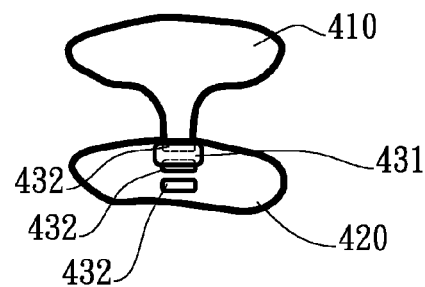
Figure 4D:
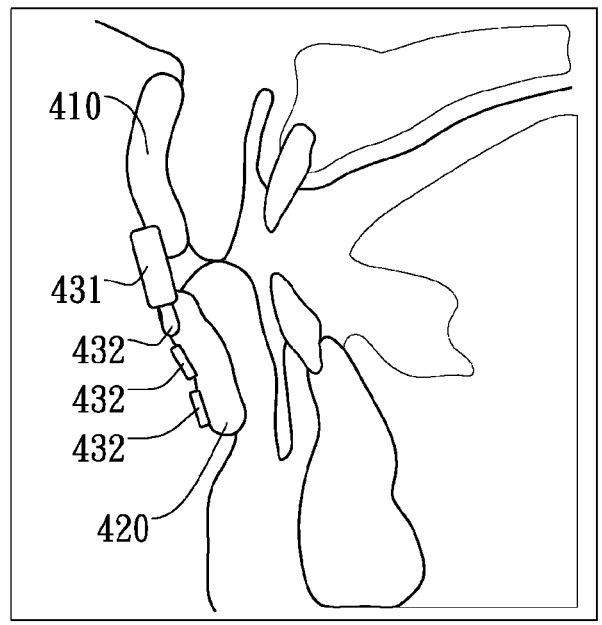
Figure 4E:
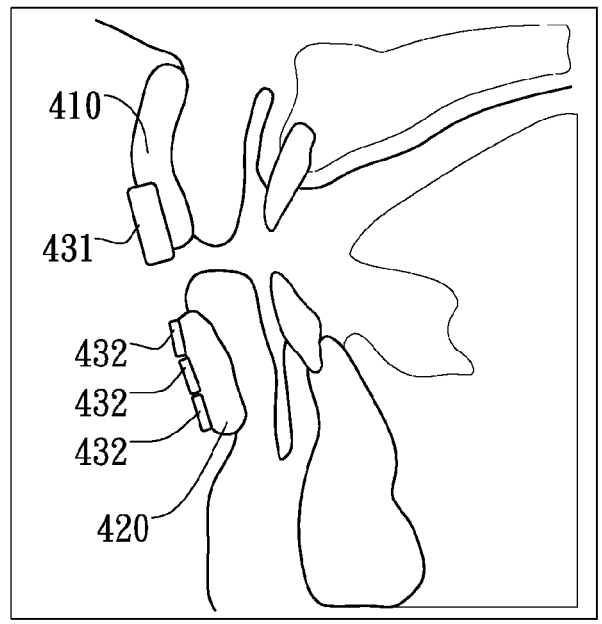

Please refer to FIG. 4A to FIG. 4E. FIG. 4A demonstrates the front view of an oral apparatus according to the fourth embodiment of the present invention. The oral apparatus comprises of an upper attaching component 410 and a lower component 420. The attaching components can be of various thickness and flexibility, and is capable of adhering firmly to the skin. Potential materials of the upper attaching component 410 and the lower component 420 include silicone, flexible plastic, latex, gel, hydrogel, acrylic gel as well as other materials coated with an adhesive substance. The adhesive upper and lower attaching components 410 and 420 can be temporarily attached to the skin around the upper and lower lips, respectively. The oral apparatus also has a mechanical connector 430 to control the distance between the upper attaching component 410 and the lower attaching component 420 in order to close the mouth. The upper and lower attaching components 410, 420 may only be applied to lip region away from the opening of the mouth to allow for the mouth to open. The closing of the mouth will be attained by the lips with the help of the pulling force exerted by the mechanical connector 430 to the upper and lower attaching components 410 and 420. As shown in FIG. 4B, the connector may comprise of a female connector 431 on one attaching component and a male connector 432 on the other attaching component so that the connectors can be engaged and disengaged to close and release the mouth. The male connector 432 may compose of multiple identical connectors to allow for anatomical difference. It can be adjusted by users to accommodate thicker or thinner lips or provide tighter or looser mouth closing as desired, as shown in FIG. 4C. The opening of mouth is not occluded by the upper and lower attaching components 410, 420 of the oral apparatus which may allow the user to exhale air through the mouth even when the male and female connectors 431 and 432 are engaged. Also the user can temporarily manually disengage the connector assembly to allow the user to drink water, speak or perform other activities. FIG. 4D and FIG. 4E demonstrate the side view of the engaged and disengaged apparatus respectively. The present invention can be used in combination with constant positive airway pressure devices, oral appliances, or other sleep apnea therapies to prevent mouth breathing.

Figure 5A:
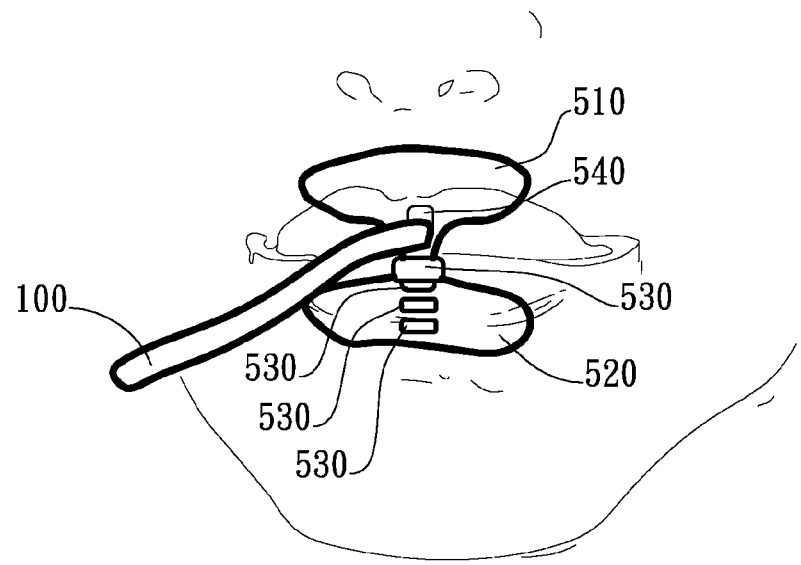
FIG. 5A and FIG. 5D show schematic diagrams of an oral apparatus according to the fifth embodiment of the present invention to use upper and lower attaching components with adjustable mechanical connectors to close the mouth while delivering oral negative pressure.
Figure 5B:
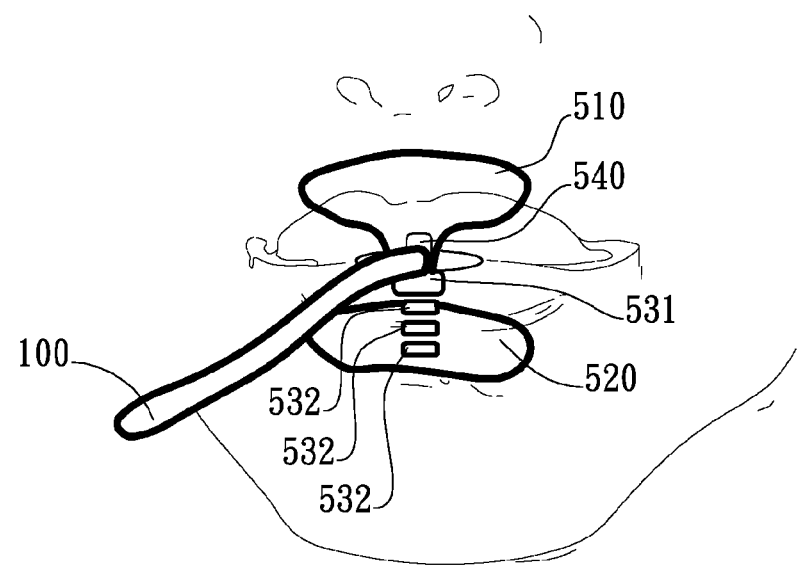
Figure 5C:
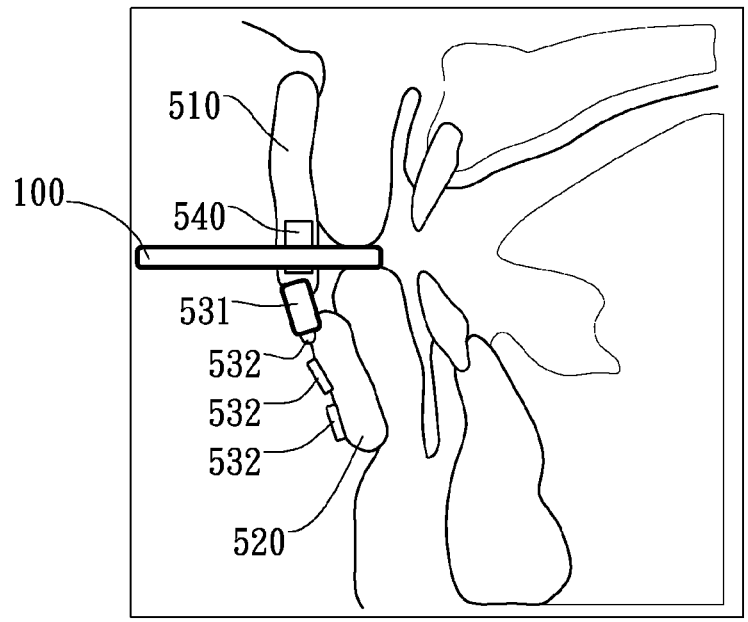
Figure 5D:
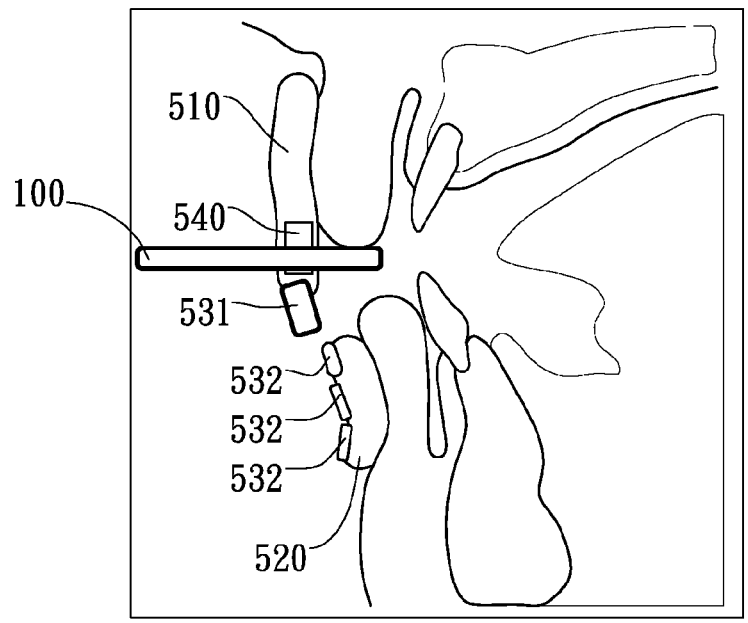

Please refer to FIG. 5A to FIG. 5D. FIG. 5A demonstrates the front view of an oral apparatus according to the fifth embodiment of the present invention. The oral apparatus comprises of an upper attaching component 510 and a lower attaching component 520. The attaching components can be of various thickness and flexibility, and is capable of adhering firmly to the skin. Potential materials of the upper attaching component 510 and the lower attaching component 520 include silicone, flexible plastic, latex, gel, hydrogel, acrylic gel as well as other materials coated with an adhesive substance. One of the attaching components may have a conduit engaging slot 540 and a fluid conduit 100 can be attached to the conduit engaging slot 540. The fluid conduit 100 is connected to a negative pressure source 100 (not shown) on one end and interfaces with the oral cavity on the other end. The fluid conduit 100 may slide up or down along the conduit engaging slot 540 to accommodate variation of distance between the mouth opening and the attaching component. The adhesive upper and lower attaching components 510 and 520 can be temporarily attached to the skin around the upper and lower lips, respectively. The oral apparatus also has a mechanical connector 530 to control the distance between the upper attaching component 510 and the lower attaching component 520 in order to close the mouth. The upper and lower attaching components 510, 520 may only be applied to lip region away from the opening of the mouth to allow for the mouth to open. The closing of the mouth will be attained by the lips with the help of the pulling force exerted by the mechanical connector 530 to the upper and lower attaching components 510 and 520. As shown in FIG. 5B, the connector may comprise of a female connector 531 on one attaching component and a male connector 532 on the other attaching component so that the connectors can be engaged and disengaged to close and release the mouth. The male connector 532 may have several identical male connectors to allow for anatomical difference. It can be adjusted by users to accommodate thicker or thinner lips or provide tighter or looser mouth closing as desired. The opening of mouth is not occluded by the upper and lower attaching components of the oral apparatus which may allow the user to exhale air through the mouth even when the male and female connectors 531 and 532 are engaged. Also the user can temporarily manually disengage the connector assembly to allow the user to drink water, speak or perform other activities. FIG. 5C and FIG. 5D demonstrate the side view of the engaged and disengaged apparatus respectively. Once the two attaching components, 510 and 520, and the fluid conduit 100 are physically engaged with the conduit engaging slot 540, the negative pressure source can draw air out of oral cavity and thus produce a negative pressure environment to pull the tongue, soft palate and other soft tissue forward to maintain the airway patency reducing snoring and apnea episodes.

Figure 6A:
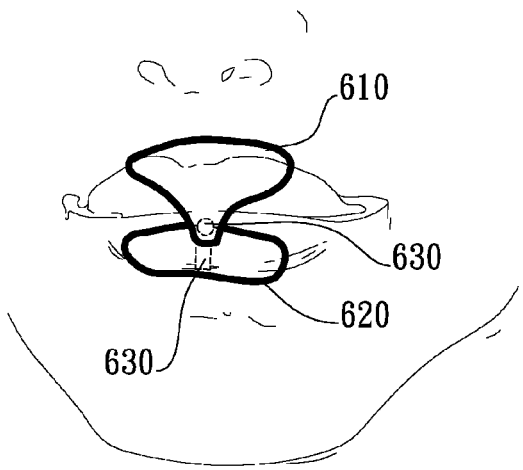
FIG. 6A to FIG. 6E show schematic diagrams of an oral apparatus according to the sixth embodiment of the present invention to use upper and lower attaching components with magnetic connectors to close the mouth.
Figure 6B:
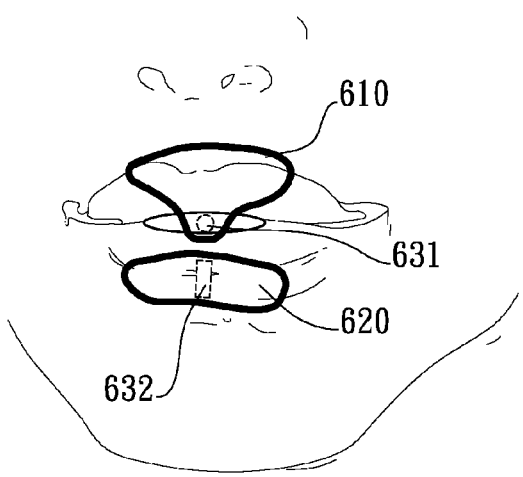
Figure 6C:
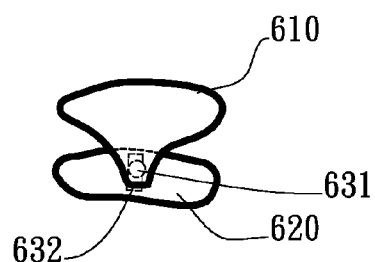
Figure 6D:
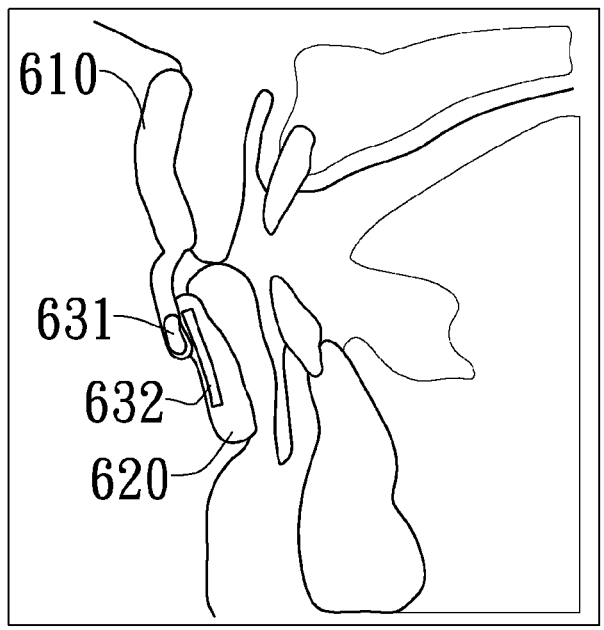
Figure 6E:
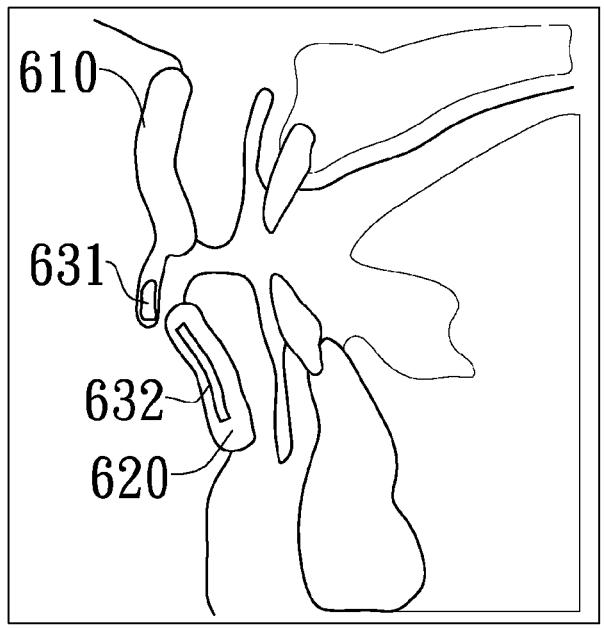

Please refer to FIG. 6A to FIG. 6E. FIG. 6A demonstrates the front view of an oral apparatus according to the sixth embodiment of the present invention. The oral apparatus comprises of an upper attaching component 610 and a lower attaching component 620. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. The adhesive upper and lower attaching components 610 and 620 can be temporarily attached to the skin around the upper and lower lips, respectively. The oral apparatus also has a magnetic connector 630 to control the distance between the upper attaching component 610 and the lower attaching component 620 in order to close the mouth. The upper and lower attaching components 610, 620 may only be applied to lip region away from the opening of the mouth to allow for the mouth to open. The closing of the mouth will be attained by the lips with the help of the pulling force exerted by the magnetic connector 630 to the upper and lower attaching components 610 and 620. As shown in FIG. 6B, the magnetic connector 630 may consist of a small magnet 631 on one attaching component and a small paramagnetic or magnetic strip 632 on the other attaching component so that the connectors can be engaged and disengaged to close and release the mouth. The paramagnetic or magnetic strip 632 is elongated in shape to have a longitudinal magnetic connection region to allow for anatomical difference. It can be adjusted by users to accommodate thicker or thinner lips or provide tighter or looser mouth closing as desired, as shown in FIG. 6C. The opening of mouth is not occluded by the upper and lower attaching components 610, 620 of the oral apparatus which may allow the user to exhale air through the mouth even when the two connectors 631 and 632 are engaged. Also the user can temporarily manually disengage the connector assembly to allow the user to drink water, speak or perform other activities. FIG. 6D and FIG. 6E demonstrate the side view of the engaged and disengaged apparatus respectively. The present invention can be used in combination with constant positive airway pressure devices, oral appliances, or other sleep apnea therapies to prevent mouth breathing.

Figure 7A:
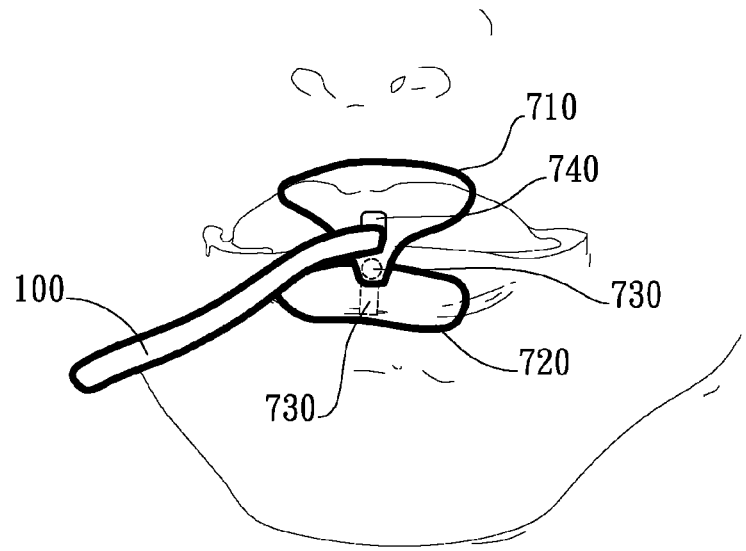
FIG. 7A to FIG. 7D show schematic diagrams of an oral apparatus according to the seventh embodiment of the present invention to use upper and lower attaching components with magnetic connectors to close the mouth while delivering oral negative pressure.
Figure 7B:
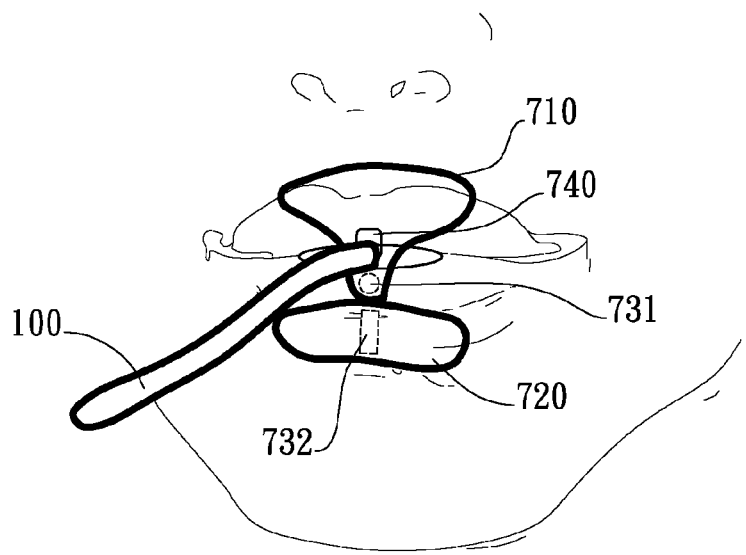
Figure 7C:
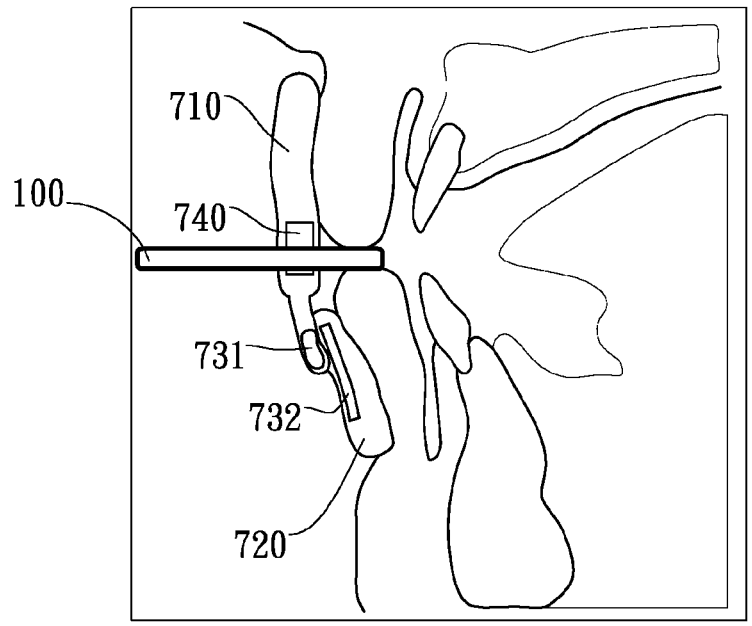
Figure 7D:
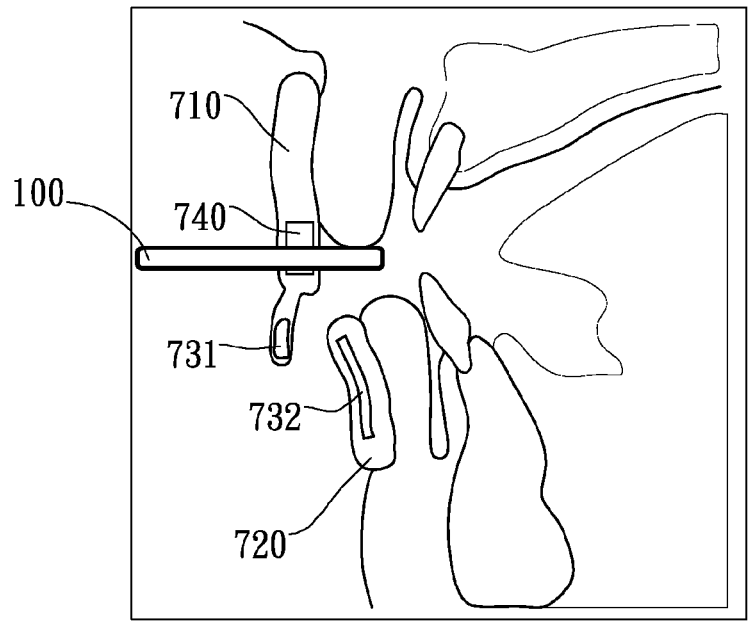

Please refer to FIG. 7A to FIG. 7D. FIG. 7A demonstrates the front view of an oral apparatus according to the seventh embodiment of the present invention. The oral apparatus comprises of an upper attaching component 710 and a lower attaching component 720. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. One of the attaching components may have a conduit engaging slot 740 and a fluid conduit 100 can be attached to the conduit engaging slot 740. The fluid conduit 100 is connected to a negative pressure source (not shown) on one end and interfaces with the oral cavity on the other end. The fluid conduit 100 may slide up or down along the conduit engaging slot 740 to accommodate variation of distance between the mouth opening and the attaching component. The adhesive upper and lower attaching components 710 and 720 can be temporarily attached to the skin around the upper and lower lips, respectively. The oral apparatus also has a magnetic connector 730 to control the distance between the upper attaching component 710 and the lower attaching component 720 in order to close the mouth. The upper and lower attaching components 710, 720 may only be applied to lip region away from the opening of the mouth to allow for the mouth to open. The closing of the mouth will be attained by the lips with the help of the pulling force exerted by the magnetic connector 730 to the upper and lower attaching components 710 and 720. As shown in FIG. 7B, the connector may consist of a small magnet 731 on one attaching component and a small paramagnetic or magnetic strip 732 on the other attaching component so that the connectors can be engaged and disengaged to close and release the mouth. The paramagnetic or magnetic strip 732 is elongated in shape to have a longitudinal magnetic connection region to allow for anatomical difference. It can be adjusted by users to accommodate thicker or thinner lips or provide tighter or looser mouth closing as desired. The opening of mouth is not occluded by the upper and lower attaching components 710, 720 of the oral apparatus which may allow the user to exhale air through the mouth even when the two connectors 731 and 732 are engaged. Also the user can temporarily manually disengage the connector assembly to allow the user to drink water, speak or perform other activities. FIG. 7C and FIG. 7D demonstrate the side view of the engaged and disengaged apparatus respectively. Once the two attaching components, 710 and 720, and the fluid conduit 100 are physically engaged with the conduit engaging slot 740, the negative pressure source can draw air out of oral cavity and thus produce a negative pressure environment to pull the tongue, soft palate and other soft tissue forward to maintain the airway patency reducing snoring and apnea episodes.

Figure 8A:
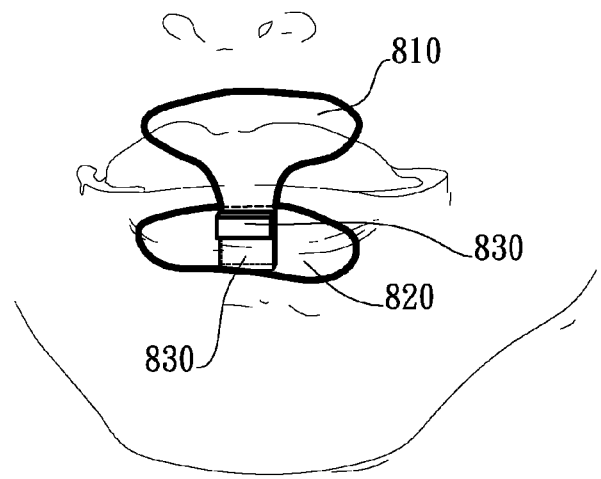
FIG. 8A to FIG. 8E show schematic diagrams of an oral apparatus according to the eighth embodiment of the present invention to use upper and lower attaching components with friction driven connectors to close the mouth.
Figure 8B:
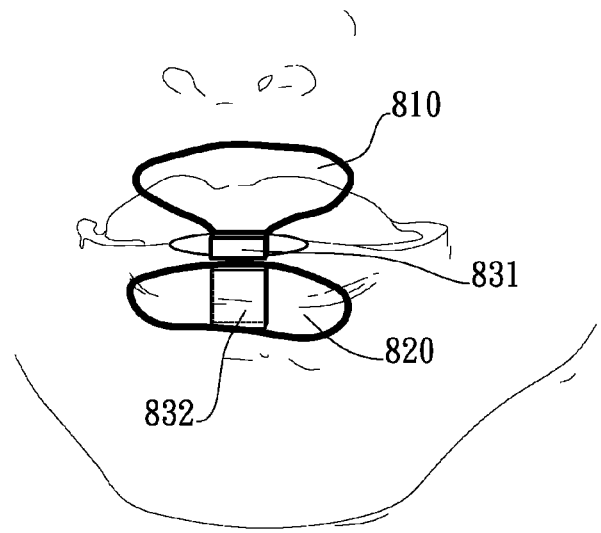
Figure 8C:
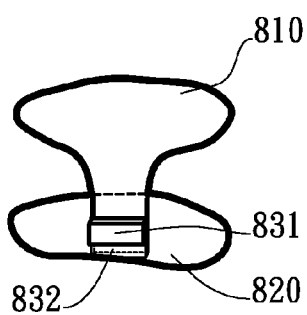
Figure 8D:
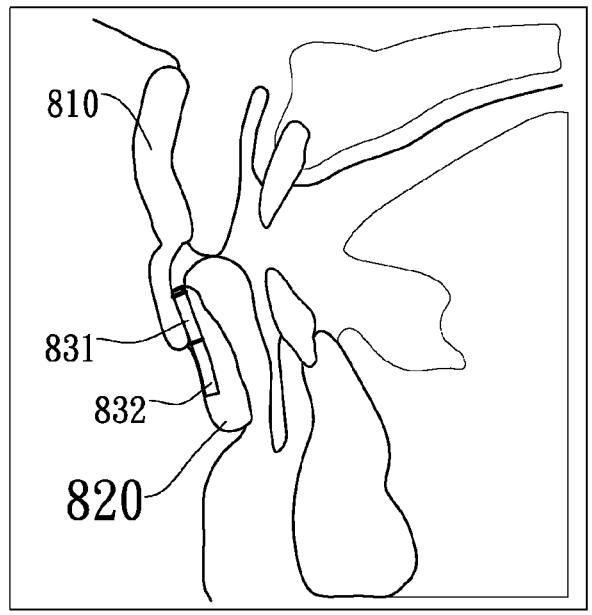
Figure 8E:
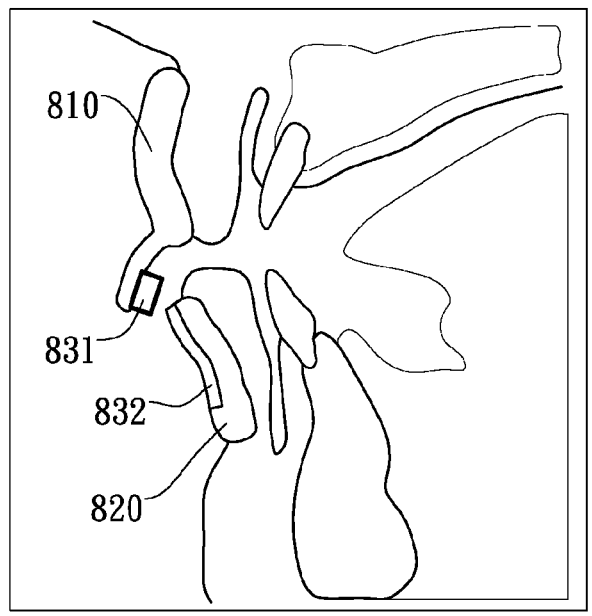

Please refer to FIG. 8A to FIG. 8E. FIG. 8A demonstrates the front view of an oral apparatus according to the eighth embodiment of the present invention. The oral apparatus comprises of an upper attaching component 810 and a lower attaching component 820. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. The adhesive upper and lower attaching components 810 and 820 can be temporarily attached to the skin around the upper and lower lips, respectively. The oral apparatus also has a frictional connector 830 to control the distance between the upper attaching component 810 and the lower attaching component 820 in order to close the mouth. The upper and lower attaching components 810, 820 may only be applied to lip region away from the opening of the mouth to allow for the mouth to open. The closing of the mouth will be attained by the lips with the help of the pulling force exerted by the frictional connector 830 to the upper and lower attaching components 810 and 820. As shown in FIG. 8B, the connector may consist of a two-part connector comprised of a protruding structure 831 on one attaching component and a sunken structure 832 on the other attaching component so that the connectors can be engaged and disengaged to close and release the mouth. When the protruding structure 831 is inserted into the sunken structure 832, frictional force locks the two attaching components in place. The protruding structure 831 can be inserted into the sunken structure 832 at various locations to allow for anatomical difference. It can be adjusted by users to accommodate thicker or thinner lips or provide tighter or looser mouth closing as desired, as shown in FIG. 8C. The opening of mouth is not occluded by the upper and lower attaching components 810, 820 of the oral apparatus which may allow the user to exhale air through the mouth even when the two connectors 831 and 832 are engaged. Also the user can temporarily manually disengage the connector assembly to allow the user to drink water, speak or perform other activities. FIG. 8D and FIG. 8E demonstrate the side view of the engaged and disengaged apparatus respectively. The present invention can be used in combination with constant positive airway pressure devices, oral appliances, or other sleep apnea therapies to prevent mouth breathing.

Figure 9A:
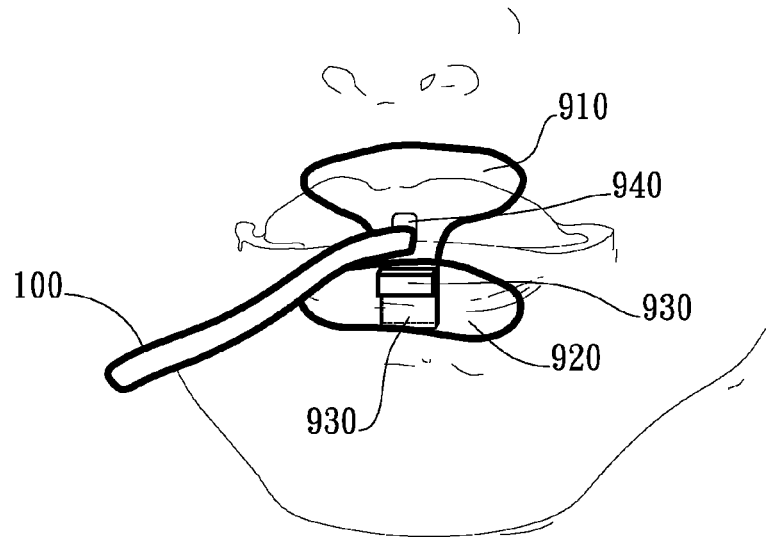
FIG. 9A to FIG. 9E show schematic diagrams of an oral apparatus according to the ninth embodiment of the present invention to use upper and lower attaching components with friction driven connectors to close the mouth while delivering oral negative pressure.
Figure 9B:
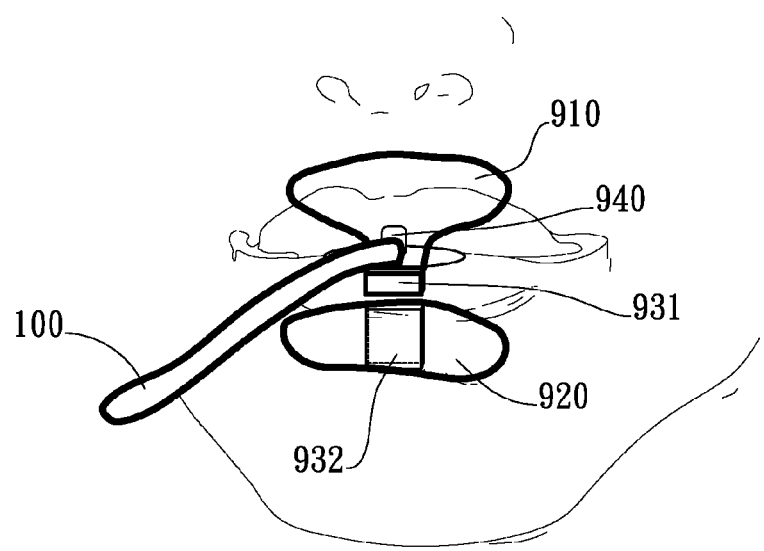
Figure 9C:
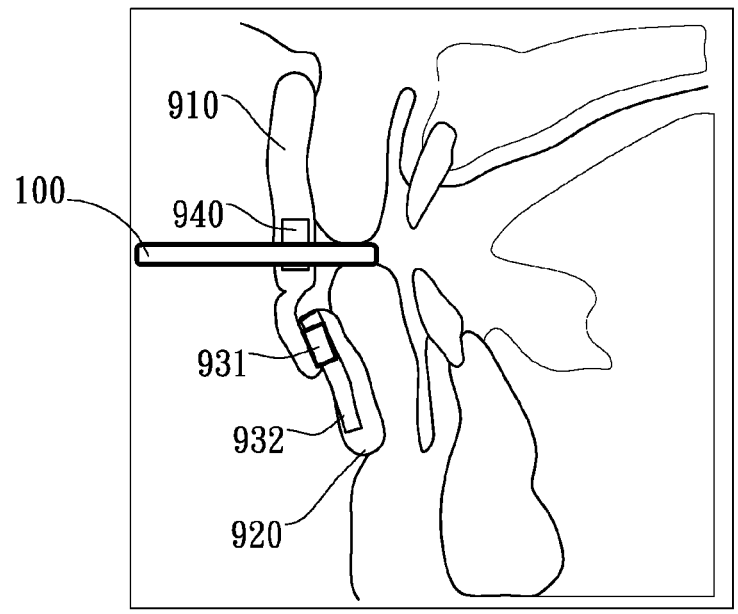
Figure 9D:
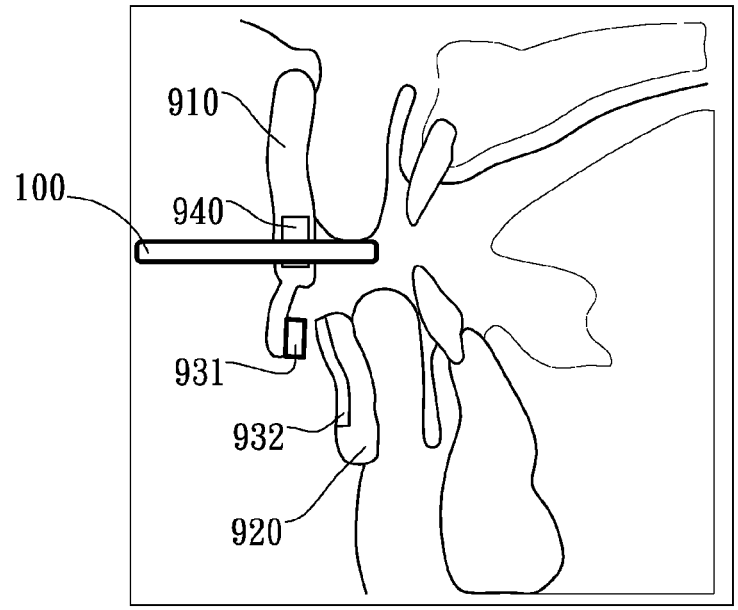
Figure 9E:
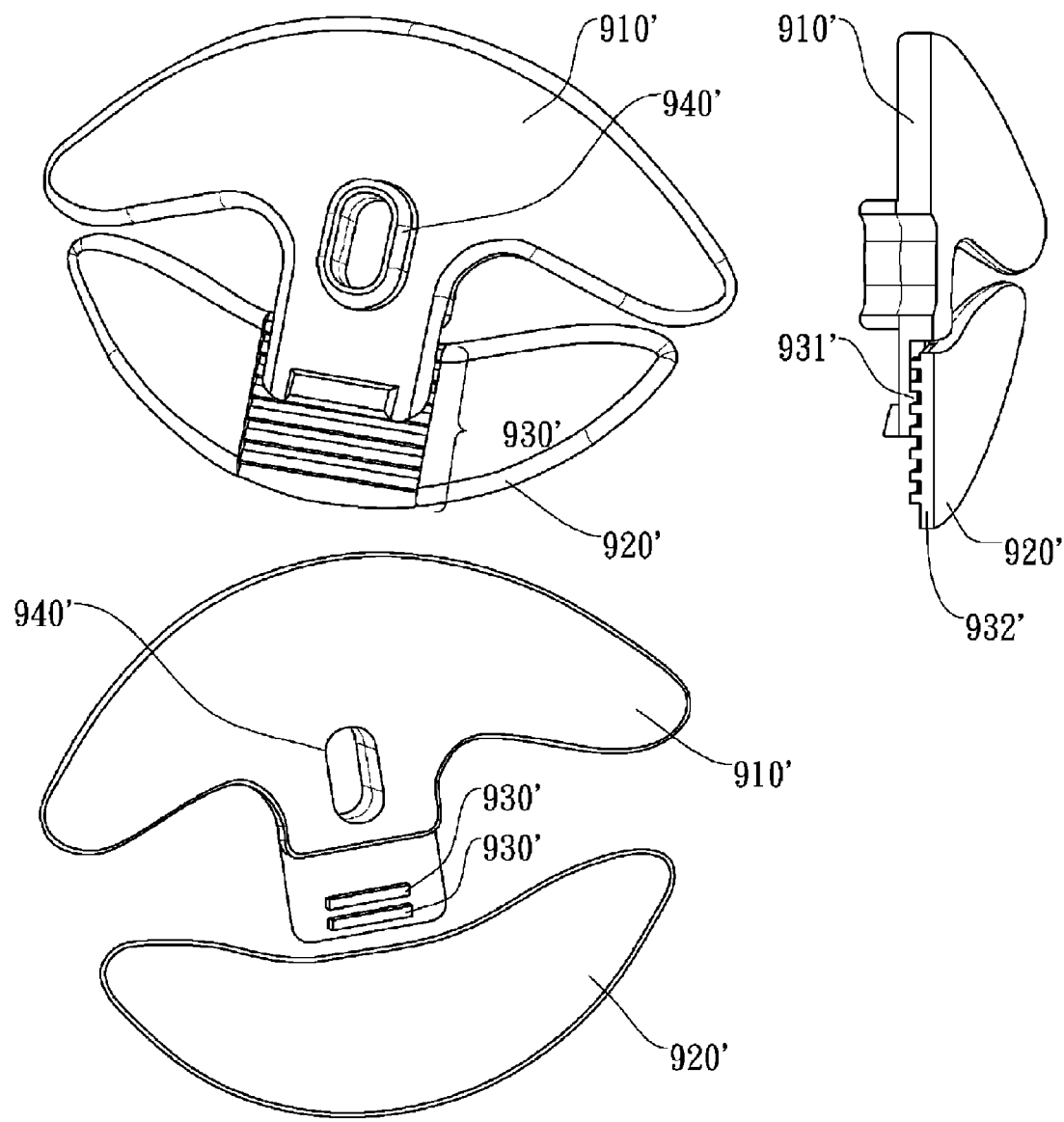

Please refer to FIG. 9A to FIG. 9E. FIG. 9A demonstrates the front view of an oral apparatus according to the ninth embodiment of the present invention. The oral apparatus comprises of an upper attaching component 910 and a lower attaching component 920. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. One of the attaching components may have a conduit engaging slot 940 and a fluid conduit 100 can be attached to the conduit engaging slot 940. The fluid conduit 100 is connected to a negative pressure source (not shown) on one end and interfaces with the oral cavity on the other end. The fluid conduit 100 may slide up or down along the conduit engaging slot 940 to accommodate variation of distance between the mouth opening and the attaching component. The adhesive upper and lower attaching components 910 and 920 can be temporarily attached to the skin around the upper and lower lips, respectively. The oral apparatus also has a frictional connector 930 to control the distance between the upper attaching component 910 and the lower attaching component 920 in order to close the mouth. The upper and lower attaching components 910, 920 may only be applied to lip region away from the opening of the mouth to allow for the mouth to open. The closing of the mouth will be attained by the lips with the help of the pulling force exerted by the frictional connector 930 to the upper and lower attaching components 910 and 920. As shown in FIG. 9B, the connector may consist of a protruding structure 931 on one attaching component and a sunken structure 932 on the other attaching component so that the connectors can be engaged and disengaged to close and release the mouth. When the protruding structure 931 is inserted into the sunken structure 932, frictional force locks the two attaching components in place. The protruding structure 931 can be inserted into the sunken structure 932 at various locations to allow for anatomical difference. It can be adjusted by users to accommodate thicker or thinner lips or provide tighter or looser mouth closing as desired. The opening of mouth is not occluded by the upper and lower attaching components 910, 920 of the oral apparatus which may allow the user to exhale air through the mouth even when the two connectors 931 and 932 are engaged. Also the user can temporarily manually disengage the connector assembly to allow the user to drink water, speak or perform other activities. FIG. 9C and FIG. 9D demonstrate the side view of the engaged and disengaged apparatus respectively. Once the two attaching components, 910 and 920, and the fluid conduit 100 are physically engaged with the conduit engaging slot 940, the negative pressure source can draw air out of oral cavity and thus produce a negative pressure environment to pull the tongue, soft palate and other soft tissue forward to maintain the airway patency reducing snoring and apnea episodes. FIG. 9E shows front, back, and cross-sectional views of another example of oral apparatus with attaching components, 910' and 920', and a frictional connector 930'. One of the attaching components 910' and 920' may have a conduit engaging slot 940' and a fluid conduit 100 can be attached to the conduit engaging slot 940'. The frictional connector 930' may comprise of a protruding structure 931' on one attaching component and a periodic sunken structure 932' on the other attaching component so that the frictional connector 930' can be engaged and disengaged to close and release the mouth. When the protruding structure 931' is inserted into part of the periodic sunken structure 932', frictional force locks the two attaching components in place. The protruding structure 931' can be inserted into the periodic sunken structure 932' at various locations to allow for the anatomical difference.

Figure 10A:
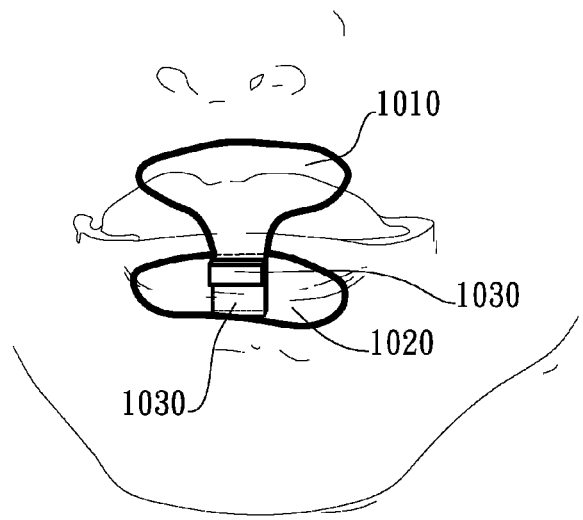
FIG. 10A and FIG. 10E show schematic diagrams of an oral apparatus according to the tenth embodiment of the present invention to use upper and lower attaching components with adhesive connectors to close the mouth.
Figure 10B:
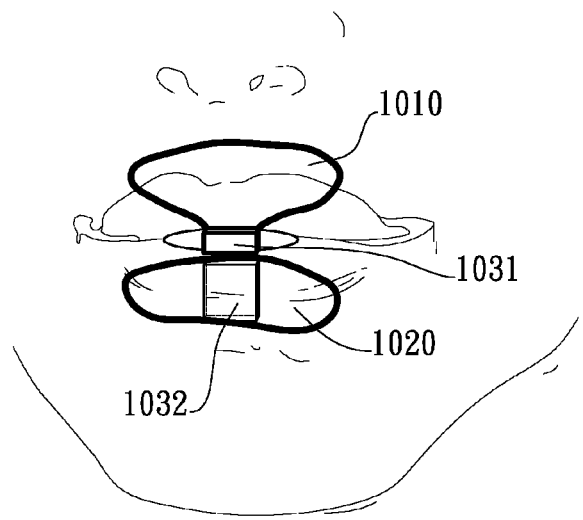
Figure 10C:
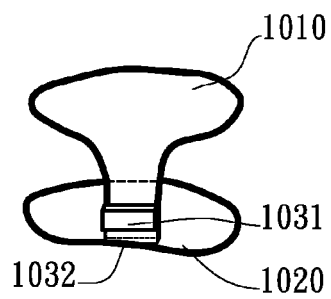
Figure 10D:
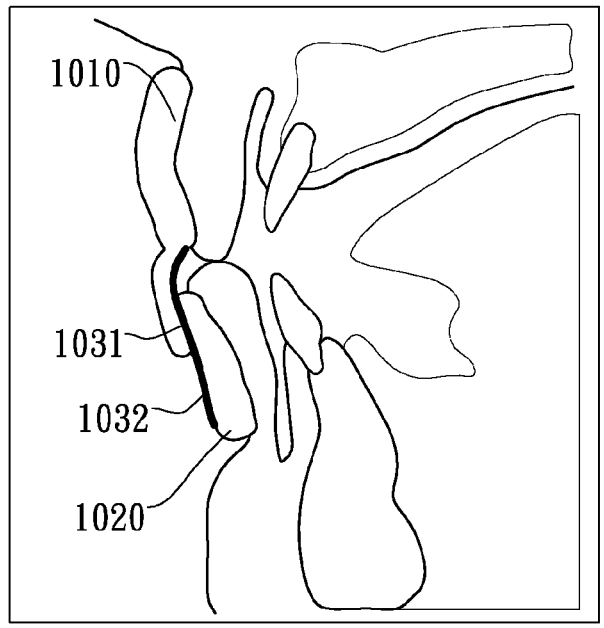
Figure 10E:
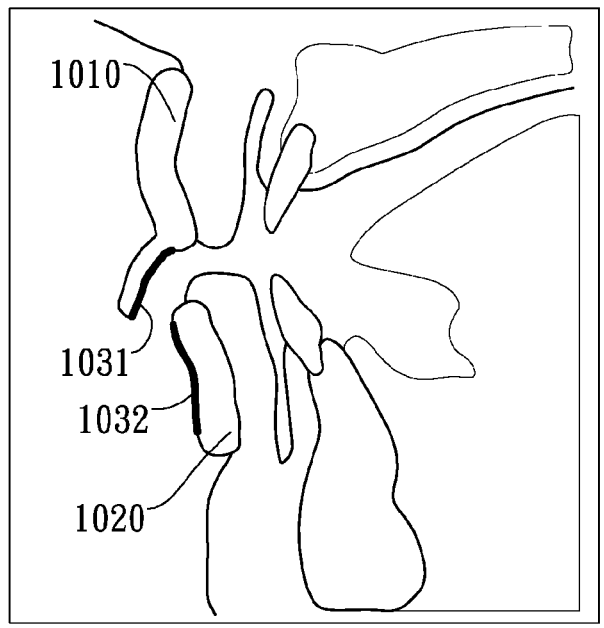

Please refer to FIG. 10A to FIG. 10E. FIG. 10A demonstrates the front view of an oral apparatus according to the tenth embodiment of the present invention. The oral apparatus comprises of an upper attaching component 1010 and a lower attaching component 1020. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. The adhesive upper and lower attaching components 1010 and 1020 can be temporarily attached to the skin around the upper and lower lips, respectively. The oral apparatus also has an adhesive connector 1030 to control the distance between the upper attaching component 1010 and the lower attaching component 1020 in order to close the mouth. The upper and lower attaching components 1010, 1020 may only be applied to lip region away from the opening of the mouth to allow for the mouth to open. The closing of the mouth will be attained by the lips with the help of the pulling force exerted by the adhesive connector 1030 to the upper and lower attaching components 1010 and 1020. As shown in FIG. 10B, the adhesive connector 1030 may consist of two adhesive connectors 1031 and 1032. The mouth can be closed and released by engaging and disengaging the adhesive connectors 1031, 1032, respectively. The two adhesive connectors 1031 and 1032 can be connected at various locations to allow for anatomical difference. It can be adjusted by users to accommodate thicker or thinner lips or provide tighter or looser mouth closing as desired, as shown in FIG. 10C. The opening of mouth is not occluded by the upper and lower attaching components 1010, 1020 of the oral apparatus which may allow the user to exhale air through the mouth even when the two adhesive connectors 1031 and 1032 are engaged. Also the user can temporarily manually disengage the connector assembly to allow the user to drink water, speak or perform other activities. FIG. 10D and FIG. 10E demonstrate the side view of the engaged and disengaged apparatus respectively. The present invention can be used in combination with constant positive airway pressure devices, oral appliances, or other sleep apnea therapies to prevent mouth breathing.

Figure 11A:
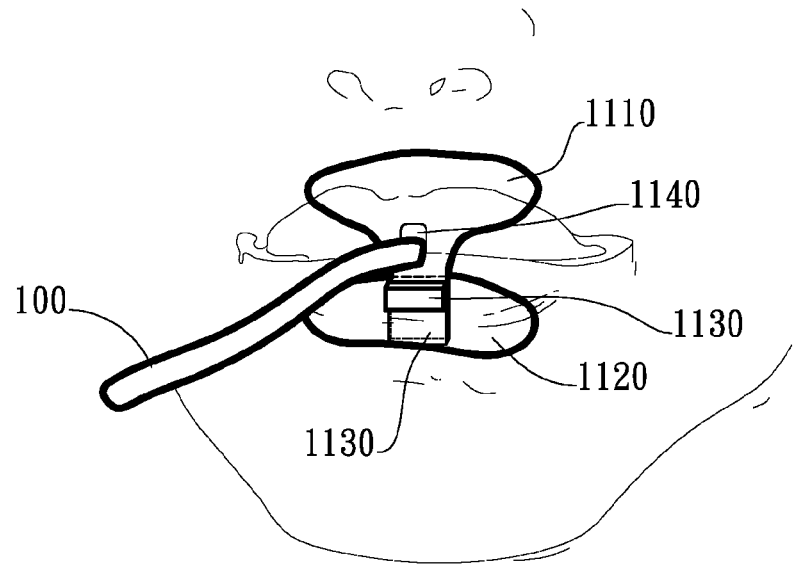
FIG. 11A and FIG. 11D show schematic diagrams of an oral apparatus according to the eleventh embodiment of the present invention to use upper and lower attaching components with adhesive connectors to close the mouth while delivering oral negative pressure.
Figure 11B:
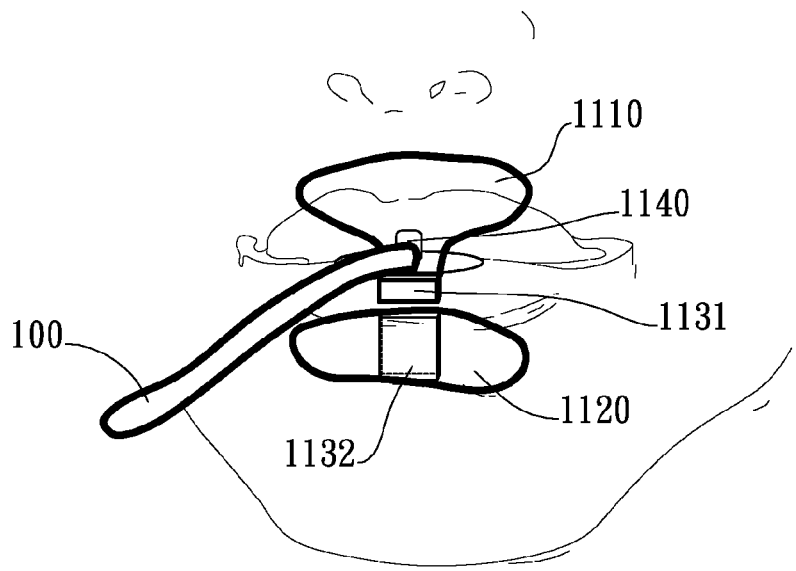
Figure 11C:
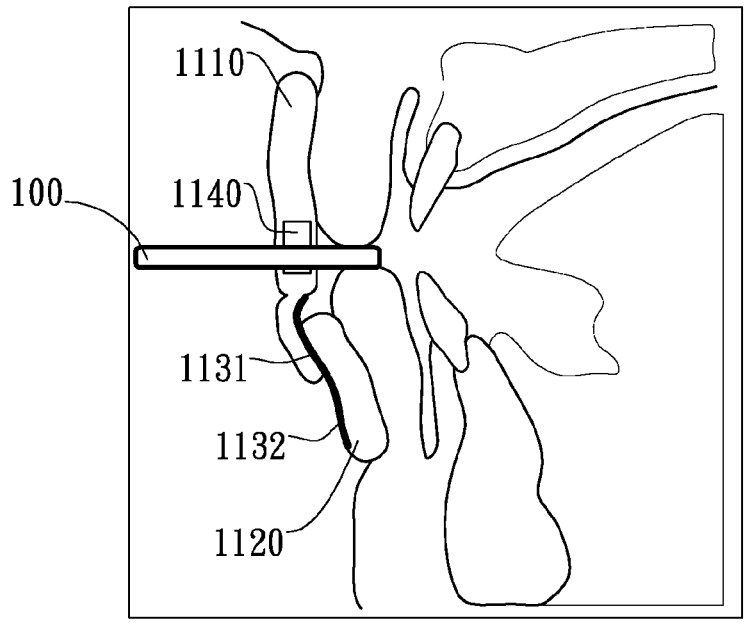
Figure 11D:
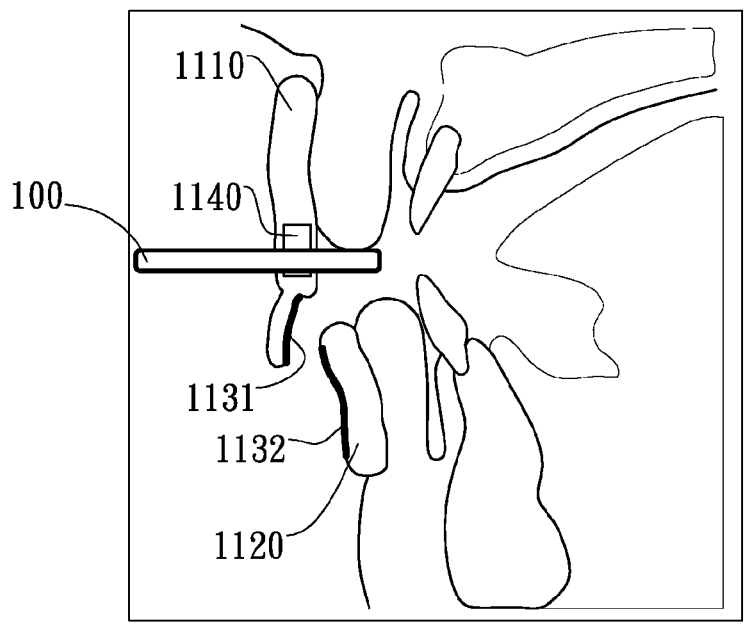

Please refer to FIG. 11A to FIG. 11D. FIG. 11A demonstrates the front view of an oral apparatus according to the eleventh embodiment of the present invention. The oral apparatus comprises of an upper attaching component 1110 and a lower attaching component 1120. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. One of the attaching components may have a conduit engaging slot 1140 and a fluid conduit 100 can be attached to the conduit engaging slot 1140. The fluid conduit 100 is connected to a negative pressure source (not shown) on one end and interfaces with the oral cavity on the other end. The fluid conduit 100 may slide up or down along the conduit engaging slot 1140 to accommodate variation of distance between the mouth opening and the attaching component. The adhesive upper and lower attaching components 1110 and 1120 can be temporarily attached to the skin around the upper and lower lips, respectively. The oral apparatus also has an adhesive connector 1130 to control the distance between upper attaching component 1110 and the lower attaching component 1120 in order to close the mouth. The upper and lower attaching components 1110, 1120 may only be applied to lip region away from the opening of the mouth to allow for the mouth to open. The closing of the mouth will be attained by the lips with the help of the pulling force exerted by the adhesive connector 1130 to the upper and lower attaching components 1110 and 1120. As shown in FIG. 11B, the connector may consist of two adhesive connectors 1131 and 1132. The mouth can be closed and released by engaging and disengaging the adhesive connectors, respectively. The two adhesive connectors 1131 and 1132 can be connected at various locations to allow for anatomical difference. It can be adjusted by users to accommodate thicker or thinner lips or provide tighter or looser mouth closing as desired. The opening of mouth is not occluded by the upper and lower attaching components 1110, 1120 of the interface which may allow the user to exhale air through the mouth even when the two adhesive connectors 1131 and 1132 are engaged. Also the user can temporarily manually disengage the connector assembly to allow the user to drink water, speak or perform other activities. FIG. 11C and FIG. 11D demonstrate the side view of the engaged and disengaged apparatus respectively. Once the two attaching components, 1110 and 1120, and the fluid conduit 100 are physically engaged with the conduit engaging slot 1140, the negative pressure source can draw air out of oral cavity and thus produce a negative pressure environment to pull the tongue, soft palate and other soft tissue forward to maintain the airway patency reducing snoring and apnea episodes.

Figure 12A:
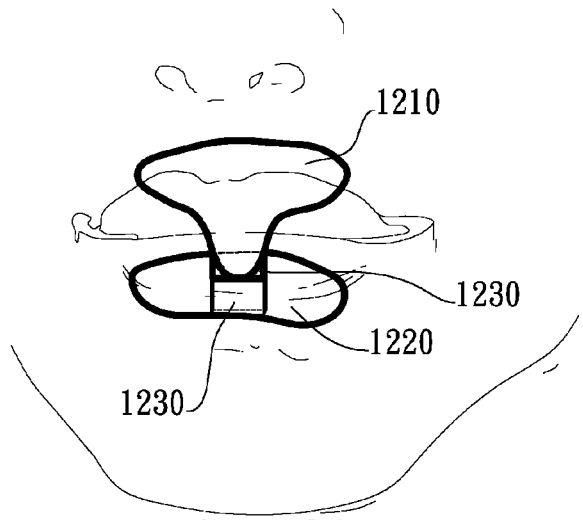
FIG. 12A to FIG. 12E show schematic diagrams of an oral apparatus according to the twelfth embodiment of the present invention to use upper and lower attaching components with non-adhesive (Dual Lock™ or loop) tapes to close the mouth.
Figure 12B:
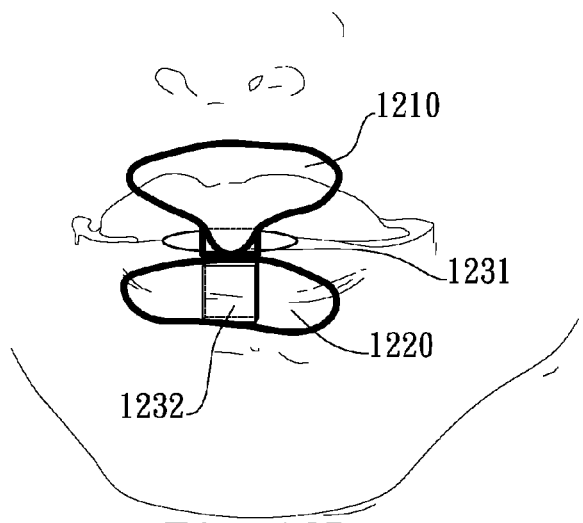
Figure 12C:
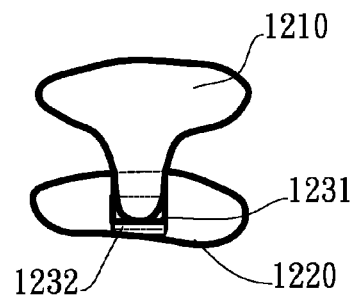
Figure 12D:
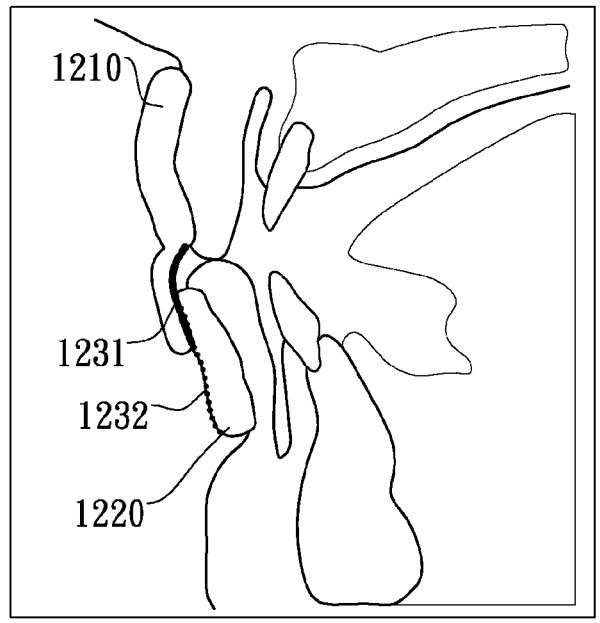
Figure 12E:
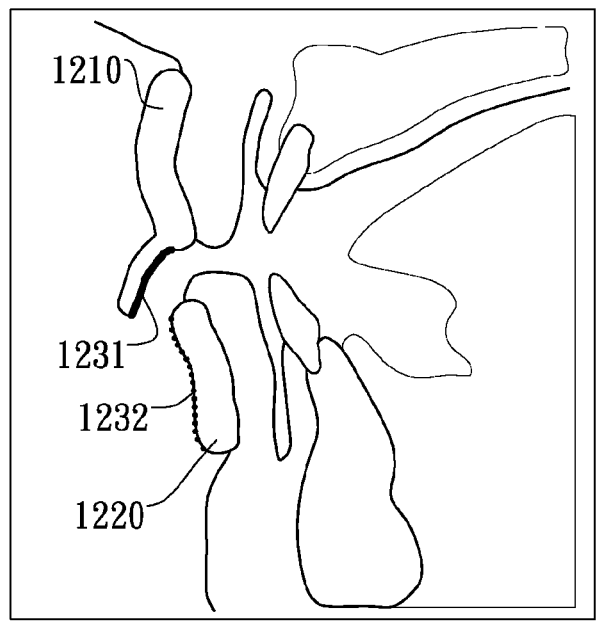

Please refer to FIG. 12A to FIG. 12E. FIG. 12A demonstrates the front view of an oral apparatus according to the twelfth embodiment of the present invention. The oral apparatus comprises of an upper attaching component 1210 and a lower attaching component 1220. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. The adhesive upper and lower attaching components 1210 and 1220 can be temporarily attached to the skin around the upper and lower lips, respectively. The oral apparatus also has a non-adhesive connector 1230 to control the distance between the upper attaching component 1210 and the lower attaching component 1220 in order to close the mouth. The upper and lower attaching components 1210, 1220 may only be applied to lip region away from the opening of the mouth to allow for the mouth to open. The closing of the mouth will be attained by the lips with the help of the pulling force exerted by the non-adhesive connector 1230 to the upper and lower attaching components 1210 and 1220. Possible mechanisms for the connector include Dual Lock™, Velcro™ loop tapes. As shown in FIG. 12B, the connector may consist of non-adhesive connectors 1231 and 1232. The mouth can be closed and released by engaging and disengaging the non-adhesive connectors 1231, 1232, respectively. The non-adhesive connectors 1231 and 1232 can be connected at various locations to allow for anatomical difference. It can be adjusted by users to accommodate thicker or thinner lips or provide tighter or looser mouth closing as desired as shown in FIG. 12C. The opening of mouth is not occluded by the upper and lower attaching components 1210, 1220 of the oral apparatus which may allow the user to exhale air through the mouth even when the two non-adhesive connectors 1231 and 1232 are engaged. Also the user can temporarily manually disengage the connector assembly to allow the user to drink water, speak or perform other activities. FIG. 12D and FIG. 12E demonstrate the side view of the engaged and disengaged apparatus respectively. The present invention can be used in combination with constant positive airway pressure devices, oral appliances, or other sleep apnea therapies to prevent mouth breathing.

Figure 13A:
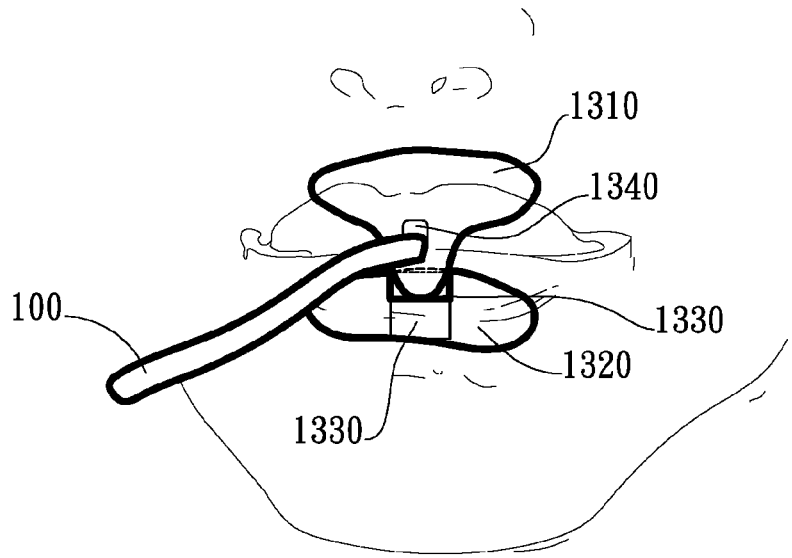
FIG. 13A to FIG. 13D show schematic diagrams of an oral apparatus according to the thirteenth embodiment of the present invention to use upper and lower attaching components with non-adhesive (Dual Lock™ or Velcro™) tapes to close the mouth while delivering oral negative pressure.
Figure 13B:
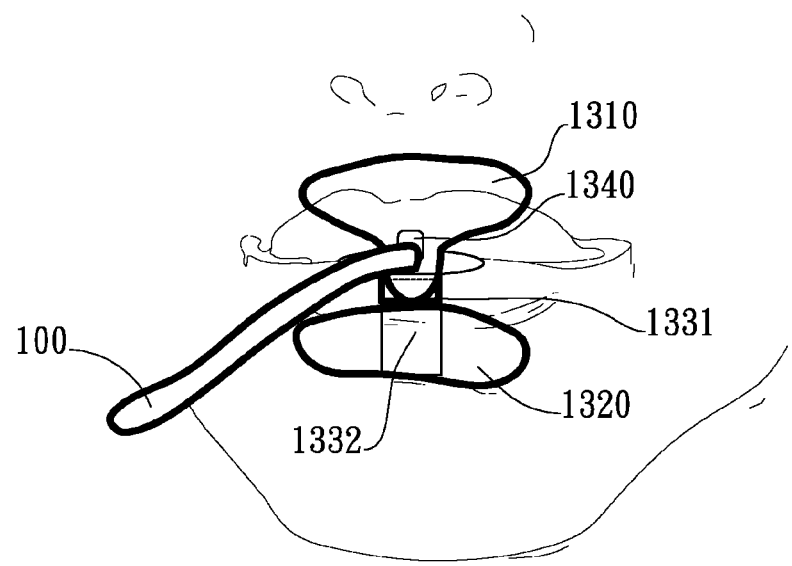
Figure 13C:
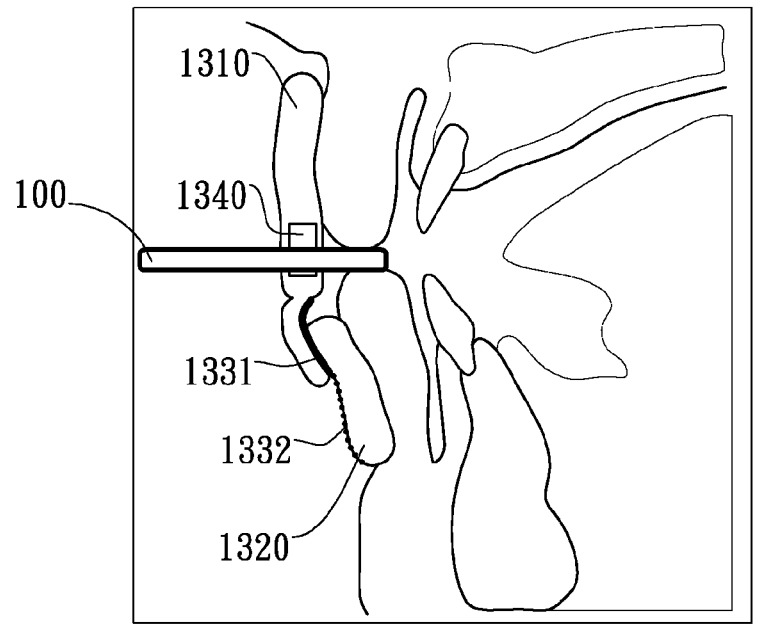
Figure 13D:
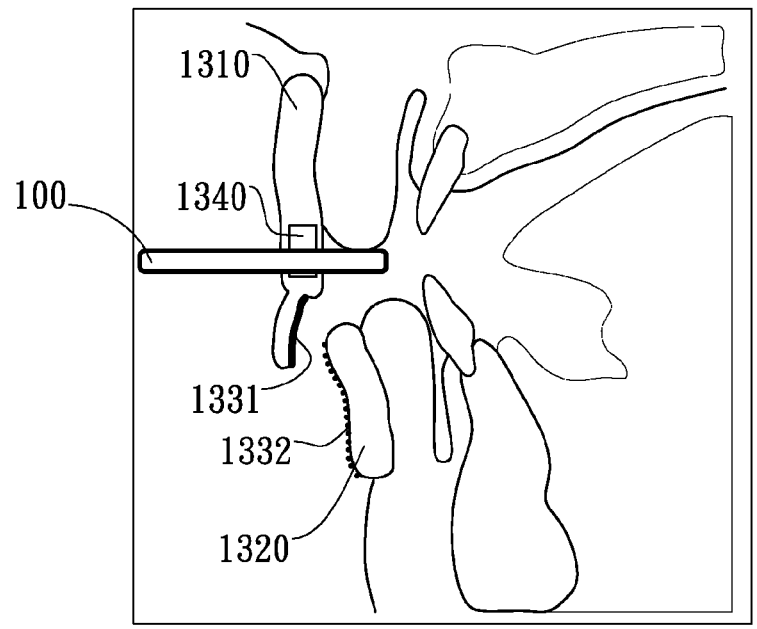

Please refer to FIG. 13A to FIG. 13D. FIG. 13A demonstrates the front view of an oral apparatus according to the thirteenth embodiment of the present invention. The oral apparatus comprises of an upper attaching component 1310 and a lower attaching component 1320. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. One of the attaching components may have a conduit engaging slot 1340 and a fluid conduit 100 can be attached to the conduit engaging slot 1340. The fluid conduit 100 is connected to a negative pressure source (not shown) on one end and interfaces with the oral cavity on the other end. The fluid conduit 100 may slide up or down along the conduit engaging slot 1340 to accommodate variation of distance between the mouth opening and the attaching component. The adhesive upper and lower attaching components 1310 and 1320 can be temporarily attached to the skin around the upper and lower lips, respectively. The oral apparatus also has a non-adhesive tape connector 1330 to control the distance between the upper attaching component 1310 and the lower attaching component 1320 in order to close the mouth. The upper and lower attaching components 1310, 1320 may only be applied to lip region away from the opening of the mouth to allow for the mouth to open. The closing of the mouth will be attained by the lips with the help of the pulling force exerted by the non-adhesive connector 1330 to the upper and lower attaching components 1310 and 1320. Possible mechanisms for the connector include Dual Lock™, Velcro™ and loop tapes. As shown in FIG. 13B, the connector may consist of non-adhesive connectors 1331 and 1332. The mouth can be closed and released by engaging and disengaging the non-adhesive connectors 1331, 1332, respectively. The two non-adhesive connectors 1331 and 1332 can be connected at various locations to allow for anatomical difference. It can be adjusted by users to accommodate thicker or thinner lips or provide tighter or looser mouth closing as desired. The opening of mouth is not occluded by the upper and lower attaching components 1310, 1320 of the oral apparatus which may allow the user to exhale air through the mouth even when the two non-adhesive connectors 1331 and 1332 are engaged. Also the user can temporarily manually disengage the non-adhesive connector assembly to allow the user to drink water, speak or perform other activities. FIG. 13C and FIG. 13D demonstrate the side view of the engaged and disengaged apparatus respectively. Once the two attaching components, 1310 and 1320, and the fluid conduit 100 are physically engaged with the conduit engaging slot 1340, the negative pressure source can draw air out of oral cavity and thus produce a negative pressure environment to pull the tongue, soft palate and other soft tissue forward to maintain the airway patency reducing snoring and apnea episodes.

Figure 14A:
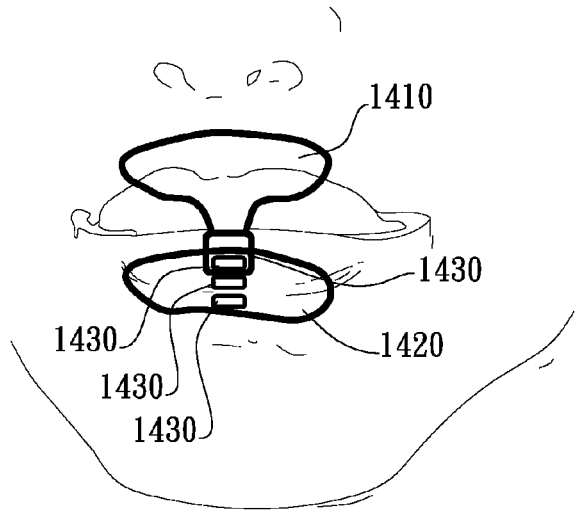
FIG. 14A to FIG. 14E show schematic diagrams of an oral apparatus according to the fourteenth embodiment of the present invention to use upper and lower attaching components with a loop 15 and hooks to close the mouth.
Figure 14B:
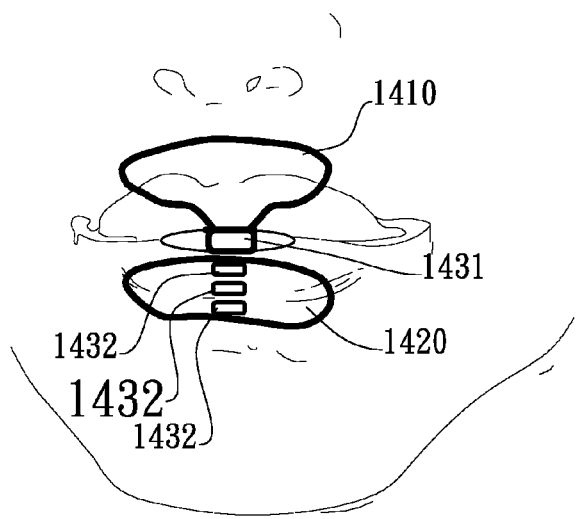
Figure 14C:
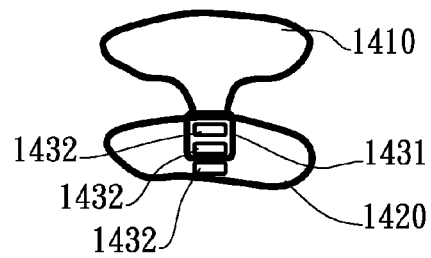
Figure 14D:
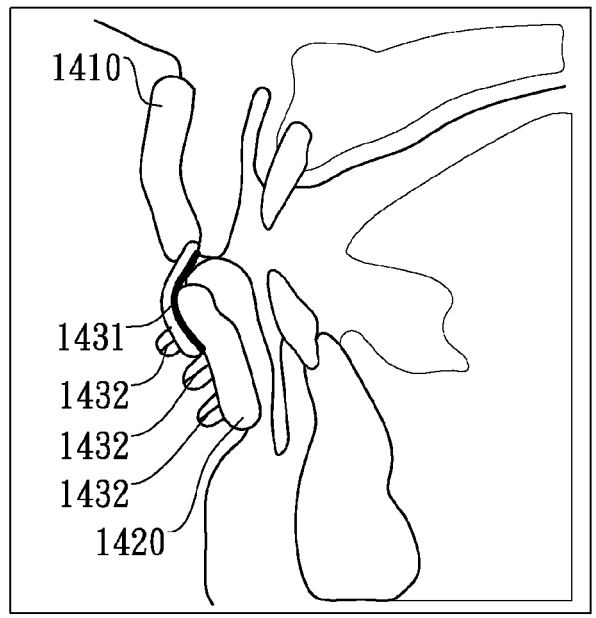
Figure 14E:
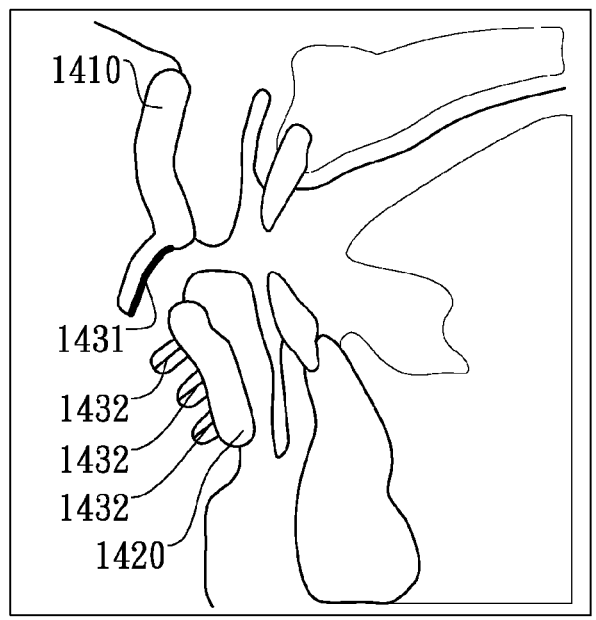

Please refer to FIG. 14A to FIG. 14E. FIG. 14A demonstrates the front view of an oral apparatus according to the fourteenth embodiment of the present invention. The oral apparatus comprises of an upper attaching component 1410 and a lower attaching component 1420. The attaching components can be of various thickness and flexibility, and is capable of adhering firmly to the skin. Potential materials of the attaching components include silicone, flexible plastic, latex, gel, hydrogel, acrylic gel as well as other materials coated with an adhesive substance. The adhesive upper and lower attaching components 1410 and 1420 can be temporarily attached to the skin around the upper and lower lips, respectively. The oral apparatus also has a hook-and-loop connector 1430 to control the distance between the upper attaching component 1410 and the lower attaching component 1420 in order to close the mouth. The upper and lower attaching components 1410, 1420 may only be applied to lip region away from the opening of the mouth to allow for the mouth to open. The closing of the mouth will be attained by the lips with the help of the pulling force exerted by the hook-and-loop connector 1430 to the upper and lower attaching components 1410 and 1420. As shown in FIG. 14B, the hook-and-loop connector 1430 may consist of a loop/band like structure 1431 and several hooks 1432. The hook-and-loop connector 1430 is used to close and release the mouth by engaging and disengaging the loop/band like structure 1431 around one of the hooks 1432 respectively. The existence of several hooks 1432 at different locations results in an adjustable apparatus for users with thicker or thinner lips to achieve an effective tighter or looser mouth closing as desired and more comfortable for the user as shown in FIG. 14C. The opening of mouth is not occluded by the upper and lower attaching components 1410, 1420 of the oral apparatus which may allow the user to exhale air through the mouth even when the loop/band like structure 1431 and one of the hooks 1432 are engaged. The user can also temporarily manually disengage the connector assembly to allow the user to drink water, speak or perform other activities. FIG. 14D and FIG. 14E demonstrate the side view of the engaged and disengaged apparatus respectively. The present invention can be used in combination with constant positive airway pressure devices, oral appliances, or other sleep apnea therapies to prevent mouth breathing.

Figure 15A:
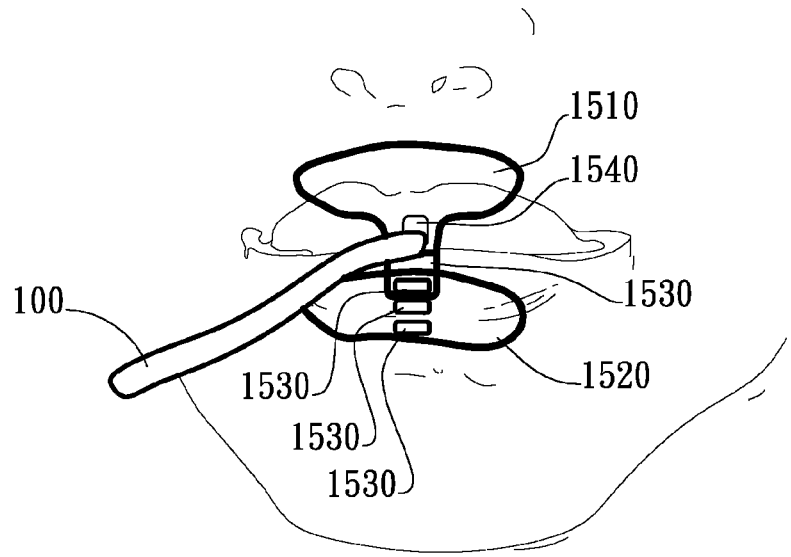
FIG. 15A to FIG. 15D show schematic diagrams of an oral apparatus according to the fifteenth embodiment of the present invention to use upper and lower attaching components with a loop and hooks to close the mouth while delivering oral negative pressure.
Figure 15B:
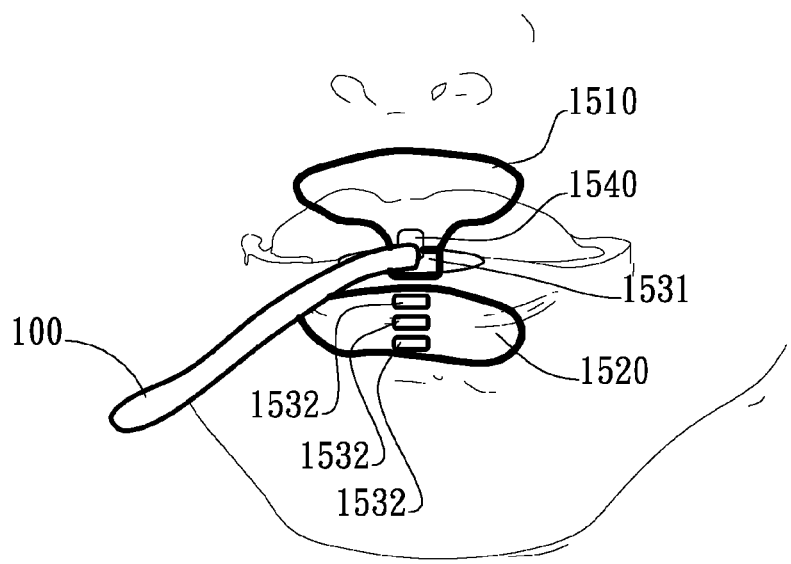
Figure 15C:
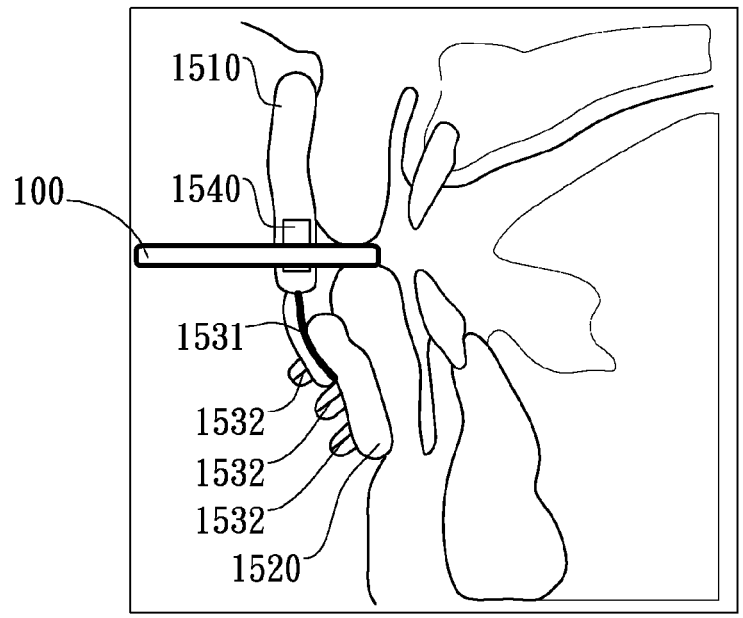
Figure 15D:
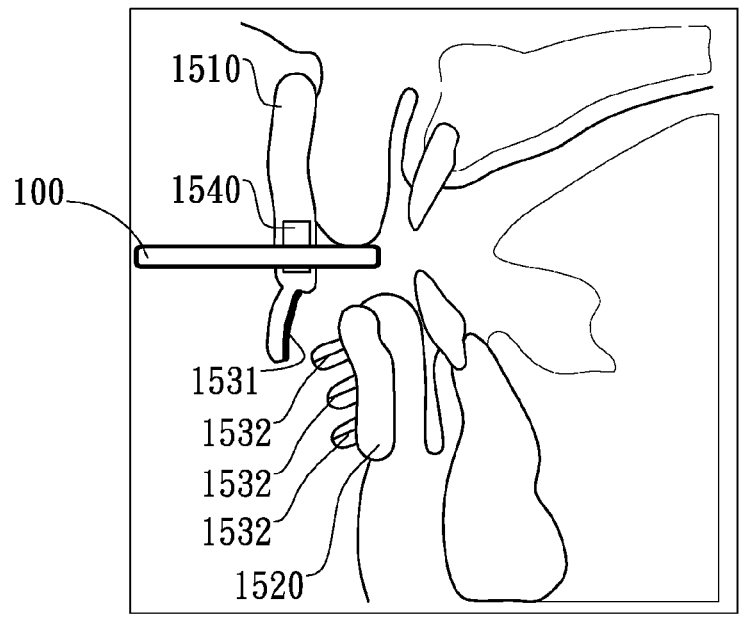

Please refer to FIG. 15A to FIG. 15D. FIG. 15A demonstrates the front view of an oral apparatus according to the fifteenth embodiment of the present invention. The oral apparatus comprises of an upper attaching component 1510 and a lower attaching component 1520. The attaching components 1510, 1520 can be of various thickness and flexibility, and is capable of adhering firmly to the skin. Potential materials of the oral apparatus include silicone, flexible plastic, latex, gel, hydrogel, acrylic gel as well as other materials coated with an adhesive substance. One of the attaching components 1510, 1520 may have a conduit engaging slot 1540 and a fluid conduit 100 can be attached to the conduit engaging slot 1540. The fluid conduit 100 is connected to a negative pressure source (not shown) on one end and interfaces with the oral cavity on the other end. The fluid conduit 100 may slide up or down along the conduit engaging slot 1540 to accommodate variation of distance between the mouth opening and the attaching component. The adhesive upper and lower attaching components 1510 and 1520 can be temporarily attached to the skin around the upper and lower lips, respectively. The oral apparatus also has a hook-and-loop connector 1530 to control the distance between the upper attaching component 1510 and the lower attaching component 1520 in order to close the mouth. The upper and lower attaching components 1510, 1520 may only be applied to lip region away from the opening of the mouth to allow for the mouth to open. The closing of the mouth will be attained by the lips with the help of the pulling force exerted by the hook-and-loop connector 1530 to the upper and lower attaching components 1510 and 1520. As shown in FIG. 15B, the hook-and-loop connector 1530 may consist of a loop/band like structure 1531 and several hooks 1532. The hook-and-loop connector 1530 is used to close and release the mouth by engaging and disengaging the loop/band like structure 1531 around one of the hooks 1532 respectively. The existence of several hooks 1532 at different locations results in an adjustable apparatus for users with thicker or thinner lips to achieve an effective tighter or looser mouth closing as desired and more comfortable for the user as shown in FIG. 15C. The opening of mouth is not occluded by the upper and lower attaching components 1510, 1520 of the oral apparatus which may allow the user to exhale air through the mouth even when the loop/band like structure 1531 and one of the hooks 1532 are engaged. Also the user can temporarily manually disengage the connector assembly to allow the user to drink water, speak or perform other activities. FIG. 15C and FIG. 15D demonstrate the side view of the engaged and disengaged apparatus respectively. Once the two attaching components 1510 and 1520, and the fluid conduit 100 are physically engaged with the conduit engaging slot 1540, the negative pressure source 100 can draw air out of oral cavity and thus produce a negative pressure environment to pull the tongue, soft palate and other soft tissue forward to maintain the airway patency reducing snoring and apnea episodes.

In addition to the specific uses described above, other embodiments and uses of the invention will be apparent to those skilled in the art from consideration of the specification and practice of the invention disclosed herein. All documents referenced herein are specifically and entirely incorporated by reference. The specification and examples should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

We claim:

1. An oral apparatus for reducing snoring and apnea episodes, comprising:
    an upper adhesive component being adapted to be adhered to regions near an upper lip;
    a lower adhesive component provided separately from the upper adhesive component and being adapted to be adhered to regions near a lower lip; and
    a connector for connecting the upper and lower adhesive components and controlling a distance between the upper and lower adhesive components.

2. The oral apparatus of claim 1, wherein the connector is adjustable with multiple connector parts.

3. A method for reducing snoring and apnea episodes comprising steps of:
    applying an upper attaching component to the skin around an upper lip of a user;
    applying a lower attaching component, separately from the upper attaching component, to the skin around a lower lip of the user; and
    connecting the upper attaching component and the lower attaching component by a connector to close the mouth to prevent breathing through the mouth.

4. The method of claim 3, further comprising:
    engaging a fluid conduit to one of the attaching components to interface a negative pressure source and the oral cavity of the user; and
    applying negative pressure to the oral cavity to maintain the upper airway patency.

5. The method of claim 4, wherein one of the attaching components comprises a conduit engaging slot, a first end of the fluid conduit passes through the conduit engaging slot, and the fluid conduit is capable of sliding up and down along the conduit engaging slot.

6. The method of claim 3, wherein the connector comprises at least one pair of magnets or a magnet and a paramagnetic component.

7. The method of claim 6, wherein one of the components of the connector is in a form of magnetic or paramagnetic strips.

8. The method of claim 3, wherein the connector is a non-adhesive connector.

9. The method of claim 8, wherein the non-adhesive connector comprises two-part non-adhesive tapes in a form of hook and loop tapes.

10. The method of claim 3, wherein the connector is a loop-and-hook connector.

11. The method of claim 10, wherein the loop-and-hook connector comprises at least one loop part and one hook part, wherein the hook part has at least one hook.

12. The method of claim 3, wherein the connector comprises at least one pair of matching connectors.

13. The method of claim 3, wherein the connector comprises at least one pair of protruding and sunken structures.

14. The method of claim 3, wherein the connector comprises at least two adhesive parts on the upper and lower attaching components, respectively.

* * * * *